(12) United States Patent
Chen

(10) Patent No.: US 8,073,549 B2
(45) Date of Patent: Dec. 6, 2011

(54) METHOD OF ELECTROGENICALLY CONTROLLING PUMP MOLECULES

(75) Inventor: Wei Chen, Tampa, FL (US)

(73) Assignee: University of South Florida, Tampa, FL (US)

(*) Notice: Subject to any disclaimer, the term of this patent is extended or adjusted under 35 U.S.C. 154(b) by 107 days.

(21) Appl. No.: 12/762,708

(22) Filed: Apr. 19, 2010

(65) Prior Publication Data

US 2010/0249757 A1 Sep. 30, 2010

Related U.S. Application Data

(63) Continuation-in-part of application No. 12/231,030, filed on Aug. 28, 2008, which is a continuation of application No. PCT/US2007/005200, filed on Feb. 28, 2007.

(60) Provisional application No. 60/767,045, filed on Feb. 28, 2006.

(51) Int. Cl.
*A61N 1/00* (2006.01)
*A61N 1/39* (2006.01)

(52) U.S. Cl. ............ 607/76; 607/1; 607/2; 607/48

(58) Field of Classification Search .............. None
See application file for complete search history.

(56) References Cited

U.S. PATENT DOCUMENTS

| 6,871,099 B1 | 3/2005 | Whitehurst et al. |
| 2007/0202506 A1 | 8/2007 | Stropp et al. |

FOREIGN PATENT DOCUMENTS

WO 2004011079 A2 2/2004

OTHER PUBLICATIONS

Markin VS et al. J. Membrane Biol 126:137-145, 1992.*
Astumian. 2003. "Adiabatic Pumping Mechanism for Ion Motive ATPases." The American Physical Society. vol. 91. No. 11. pp. 118102-1-118102-4.
Chen. 2006. "Voltage Dependence of the Carrier-Mediated Ion Transport." Physical Review E. vol. 73. pp. 021902-1-021902-7.
Liu et al. 1990. "Activation of Na+ and K+ Pumping Modes of (Na,K)-ATPase by an Oscillating Electric Field." The Journal of Biological Chemistry. vol. 265. No. 13. pp. 7260-7267.
Switkes et al. 1999. "An Adiabatic Quantum Electron Pump." Science. vol. 283. pp. 1905-1908.
Teissie et al. 1981. "Electric Field Induced Transient Pores in Phospholipid Bilayer Vesicles." Biochemistry. vol. 20. pp. 1548-1554.
Xie et al. 1994. "Recognition and Processing of Randomly Fluctuating Electric Signals by Na,K-ATPase." Biophysical Journal. vol. 67. pp. 1247-1251.
Nielsen et al. 1997. "Regulation of Na+-K+ Pump Activity in Contracting Rat Muscle." Journal of Physiology. vol. 503.3. pp. 571-581.
Blank. 1992. "Na,K-ATPase Function in Alternating Electric Fields." The FASEB Journal. vol. 6. pp. 2434-2438.
Kovacs et al., Measurement and Modification of Free Calcium Transients in Frog Skeletal Muscle Fibres by a Metallochromic Indicator Dye, J. Physiol., 1983, pp. 161-196.
Irving et al., Intrinsic Optical and Passive Electrical Properties of Cut Frog Twitch Fibers, J. Gen. Physiol., 1987, vol. 89, pp. 1-40.
Smith et al., Development of Models of Active Ion Transport for Whole-Cell Modelling: Cardiac Sodium-Potassium Pump as a Case Study, Progress in Biophysics & Molecular Biology, 2004, vol. 85, pp. 387-405.
Sokolov et al., Influence of Sodium Concentration on Changes of Membrane Capacitance Associated with the Electrogenic Ion Transport by the Na,K-ATPase, European Biophysics Journal, 1998, pp. 605-617.
Tsong, Na,K-ATPase as a Brownian Motor: Electric Field-Induced Conformational Fluctuation Leads to Uphill Pumping of Cation in the Absence of ATP, Journal of Biological Physics, 2002, vol. 28, pp. 309-325.
Hille et al., An Improved Vaseline Gap Voltage Clamp for Skeletal Muscle Fibers, The Journal of General Physiology, 1976, vol. 67, pp. 265-293.
Hui et al., Separation of QBeta and QGamma Charge Components in Frog Cut Twitch Fibers with Tetracaine, J. Gen. Physiol., 1992, vol. 99, pp. 985-1016.
Buchanan et al., Excitation- and Beta2-Agonist-Induced Activation of the Na+-F-K+ Pump in Rat Soleus Muscle, Journal of Physiology, 2002, vol. 545.1, pp. 229-240.
Chen, Evidence of Electroconformational Changes in Membrane Proteins: Field-Induced Reductions in Intra Membrane Nonlinear Charge Movement Currents, Science Direct, 2004, vol. 63, pp. 333-335.
Glynn, The Electrogenic Sodium Pump, Electrogenic Transport: Fundamental Principles and Physiological Implications, 1984, Raven Press, New York, pp. 33-48.
Hilgemann, Channel-Like Function of the Na,K Pump Probed at Microsecond Resolution in Giant Membrane Patches, Science, 1994, vol. 263, pp. 1429-1432. Albers, Biochemical Aspects of Active Transport, Annual Review Biochem., 1967, vol. 36, pp. 727-756.
Apell et al., Oxonol VI as an Optical Indicator for Membrane Potentials in Lipid Vesicles, Biochimica et Biophysica Acta/Biomembranes, 1987, vol. 903, No. 3, pp. 480-494.
Astumian et al., Nonlinear Effect of an Oscillating Electric Field on Membrane Proteins, J. Chem. Phys. 1989, vol. 91, No. 8, pp. 4891-4901.
Adrian et al., Charge Movement and Mechanical Repriming in Skeletal Muscle, J. Physiol., 1976, vol. 254, pp. 361-388.
Domaszewicz et al., Binding of the Third Na+ Ion to the Cytoplasmic Side of the Na,K-ATPase is Electrogenic, FEBS Letters, 1999, vol. 458, pp. 241-246.

(Continued)

*Primary Examiner* — Robert Landsman
(74) *Attorney, Agent, or Firm* — Michele L. Lawson; Smith & Hopen, P.A.

(57) ABSTRACT

Activation of electrogenic pump molecules can be realized by a dynamic entrainment procedure which includes two steps: synchronization of individual pump molecules to work at the same pumping pace, and gradual modulation of the synchronization frequency. Na/K pump molecules were used as an example in a physiological operating mode by applying the concept of an electronic synchrotron to the biological system. It was shown that individual Na/K pump molecules can be synchronized by a well designed oscillating electric field. The synchronized pump currents show separated inward and outward pump currents and a magnitude ratio of 3:2 reflecting stoichiometric number of the pump molecules.

18 Claims, 12 Drawing Sheets

OTHER PUBLICATIONS

Forbush, The Na+,K+-Pump, Part A: Molecular Aspects, Overview: Rose et al., Understanding the Sodium Pump and Its Relevance to Disease, Clin. Chem. 1994, vol. 40, No. 9, pp. 1674-1685.
Jorgensen eta al., Structure-Function Relationships of Na+, K+, ATP, or Mg2+ Binding and Energy Transduction in Na,K-ATPase, Biochimica et Biophysica Acta, 2001, vol. 1505, pp. 57-74. Occluded Ions and Na, K-ATPase, Prog. Clin. Biol. Res., 1988, vol. 268, pp. 229-248.
Waxman, Sodium Channel Blockers and Axonal Protection in Neuroinflammatory Disease, Brain, 2005, vol. 128, pp. 5-6.
Tsong et al., Catalytic Wheel, Brownian Motor, and Biological Energy Transduction, Aapps Bulletin, 2003, vol. 13, No. 2, pp. 12-18.
Tsong et al., Electroconformational Coupling and Membrane Protein Function, Prog. Biophys. Molec. Biol., 1987, vol. 50, pp. 1-45.
Rakowski et al., A Negative Slope in the Current-Voltage Relationship of the Na+/K+ Pump in Xenopus Oocytes Produced by Reduction of External [K+], The Journal of Membrane Biology, 1991, vol. 121, pp. 177-187.
Rakowski et al., Voltage Dependence of the Na/K Pump, the Journal of Membrane Biology, 1997, vol. 155, pp. 105-112.
Robertson et al., Frequency Dependence of Catalyzed Reactions in a Weak Oscillating Field, J. Chem. Phys., 1991, vol. 94, No. 11, pp. 7414-7418.
Sejersted et al., Dynamics and Consequences of Potassium Shifts in Skeletal Muscle and Heart During Exercise, Physiological Reviews, 2000, vol. 80, No. 4, pp. 1411-1481.
Smith et al., Factors Directly Affecting Impulse Transmission in Inflammatory Demyelinating Disease: Recent Advances in our Understanding, Current Opinion in Neurology, 2001, vol. 14, pp. 289-298.
Tatsumi et al., Na+ Dependent Ca2+ Influx Induced by Depolarization in Neurons Dissociated from Rat Nucleus Basalis, Neuroscience Letters, 1995, vol. 196, pp. 9-12.
Markin et al., Resonance Transduction of Low Level Periodic Signals by an Enzyme: An Oscillatory Activation Barrier Model, Biophys. J., 1992, vol. 61, pp. 1045-1049.
Moldovan et al., Evaluation of Na+/K+ Pump Function Following Repetitive Activity in Mouse Peripheral Nerve, Journal of Neuroscience Methods, 2006, vol. 155, pp. 161-171.
Nakao et al., [Na] and [K] Dependence of the Na/K Pump Current-Voltage Relationship in Guinea Pig Ventricular Myocytes, J. Gen. Physiol., 1989, vol. 94, pp. 539-565.
Clausen, Na+ -K+ Pump Regulation and Skeletal Muscle Contractility, Physiol. Rev., 2003, vol. 83, pp. 1269-1324.
De Weer et al., Voltage Dependence of the Na-K Pump, Am. Rev. Physiol., 1988, vol. 50, pp. 225-241.
Gadsby et al., Steady-State Current-Voltage Relationship of the Na/K Pump in Guinea Pig Ventricular Myocytes, J. Gen. Physiol., 1989, vol. 94, pp. 511-537.
Chen et al., The Asymmetric, Rectifier-Like I-V Curve of the Na/K Pump Transient Currents in Frog Skeletal Muscle Fibers, Bioelectrochemistry, 2002, vol. 56, pp. 199-202.
Chen et al., Synchronization Modulation of the Na/K Pump Molecules Can Hyperpolarize the Membrane Potential of PC12 Cells, MCB, 2006, vol. 3, No. 4, pp. 203-204.
Chen et al., Synchronization of Na/K Pump Molecules by a Train of Squared Pulses, J. Bioenerg. Biomembr., 2006, vol. 38, pp. 319-325.
Chen et al., Electrical Activation of Na/K Pumps can Increase Ionic Concentration Gradient and Membrane Resting Potential, The Journal of Membrane Biology, 2007, vol. 214, pp. 147-155.
Chen et al., Synchronization of Na/K Pump Molecules by an Oscillating Electric Field, J. Bioenerg. Biomembr., 2008, vol. 40, pp. 347-357.
Chen et al., Computer Simulation of Synchronization of Na/K Pump Molecules, J. Bioenerg. Biomembr., 2008, vol. 40, pp. 337-345.
Chen et al., Membrane Potential Hyperpolarization in Mammalian Cardiac Cells by Synchronization Modulation of Na/K Pumps, J. Membrane Biol., 2008, vol. 221, pp. 165-173.
Dando et al., Cellular Recovery from Electroporation Using Synchronisation Modulation as a Rescue Model for Electrically Injured Cells, Burns, 2008, vol. 34, pp. 1128-1136.

Apell, Toward an Understanding of Ion Transport Through the Na,K-ATPase, Ann. N.Y. Acad. Sci., 2003, vol. 986, pp. 133-140.
Astumian, Thermodynamics and Kinetics of a Brownian Motor, Science, 1997, vol. 276, pp. 917-922.
Chen et al., An Improved Double Vaseline Gap Voltage Clamp to Study Electroporated Skeletal Muscle Fibers, Biophysical Journal, 1994, vol. 66, pp. 700-709.
Xie et al., Fluctuation-Driven Directional Flow in Biochemical Cycle: Further Study of Electric Activation of Na,K Pumps, Biophysical Journal, 1997, vol. 72, pp. 2496-2502.
Kiernan et al., Effects of Membrane Polarization and Ischaemia on the Excitability Properties of Human Motor Axons, Brain, 2000, vol. 123, pp. 2542-2551.
Bamberg et al., Light-Driven Proton or Chloride Pumping by Halorhodopsin, PNAS, USA, 1993, vol. 90, pp. 639-643.
Post et al., Activation by Adenosine Triphosphate in the Phosphorylation Kinetics of Sodium and Potassium Ion Transport Adenosine Triphosphatase, The Journal of Biological Chemistry, 1972, vol. 247, No. 20, pp. 6530-6540.
Serpersu et al., Stimulation of a Ouabain-Sensitive Rb-+ Uptake in Human Erthrocytes with an External Electric Field, J. Membrane Biol., 1983, vol. 74, pp. 191-201.
Gross et al., Fluorescent Indicators of Membrane Potential: Microspectrofluorometry and Imaging, Methods in Cell Biology, 1989, vol. 30, pp. 193-218.
Blank et al., Ion Activation of the Na,K-ATPase in Alternating Currents, Bioelectrochemistry and Bioenergetics, 1990, vol. 24, pp. 51-61.
Chen, Supra-Physiological Membrane Potential Induced Conformational Changes in K+ Channel Conducting System of Skeletal Muscle Fibers, Bioelectrochemistry, 2004, vol. 62, pp. 47-56.
Schweigert et al., Voltage Dependence of the Na-K ATPase: Measurements of Ouabain-Dependent Membrane Current and Ouabain Binding in Oocytes of Xenopus Laevis, European Journal of Physiology, 1988, vol. 412, pp. 579-588.
Blank et al., The Effects of Alternating Currents on Na,K-ATPase Function, Bioelectrochemistry and Bioenergetics, 1989, vol. 22, pp. 313-322.
Tsong, Electrical Modulation of Membrane Proteins: Enforced Conformational Oscillations and Biological Energy and Signal Transductions, Annu. Rev. Biophys. Chem., 1990, vol. 19, pp. 83-106.
Weiss, Active Ion Transport, Cellular Biophysics, 1996, pp. 513.
Lauger et al., A Microscopic Model for the Current-Voltage Behaviour of the Na,K-pump, European Biophysics Journal, 1986, vol. 13, pp. 309-321.
Teissie et al., Evidence of Voltage-Induced Channel Opening in Na/K ATPase of Human Erythrocyte Membrane, The Journal of Membrane Biology, 1980, vol. 55, pp. 133-140.
Tsong et al., Absorption and Conversion of Electric Field Energy by Membrane Bound Atpases, Bioelectrochemistry and Bioenergetics, 1986, vol. 15, pp. 457-476.
Artigas et al., Ion Channel-Like Properties of the Na+/K+ Pump, Annals of the New York Academy of Sciences, 2002, vol. 976, pp. 31-40.
Chen, Synchronization of Ion Exchanges by an Oscillating Electric Field: Theory, J. Phys. Chem. B, 2008, vol. 112, pp. 10064-10070.
Chen et al., Synchronization Modulation of Na/K Pump Molecules Can Hyperpolarize the Membrane Resting Potential in Intact Fibers, J. Bioenerg. Biomembr., 2007, vol. 39, pp. 117-126.
Chen et al., Entrainment of Na/K Pumps by a Synchronization Modulation Electric Field, J. Bioenerg. Biomembr., 2007, vol. 39, pp. 331-339.
Blank, Do Electromagnetic Fields Interact with Electrons in the Na,K-ATPase?, Bioelectromagnetics, 2005, vol. 26, pp. 677-683.
European Search Report for PCT/US2007/005200 dated Nov. 23, 2010.
Stein, Energetics and the Design Principles of the Na/K-ATPase, J. Theor. Biol., 1990, vol. 147, pp. 145-159.

Hille, Ion Channels of Excitable Membranes, Third Edition, Sinauer Associates, Inc., Sunderland, Massachusetts, pp. 61-64. (2001).

Sims et al., Studies on the Mechanism by Which Cyanine Dyes Measure Membrane Potential in Red Blood Cells and Phosphatidylcholine Vesicles, Biochemistry, 1974, vol. 13, No. 16, pp. 3315-3330.

Pedemonte, Kinetic Mechanism of Inhibition of the Na+-Pump and Some of its Partial Reactions by External Na+(Na+o), J. Theor. Biol., 1988, vol. 134, pp. 165-182.

Holmgren et al., Three Distinct and Sequential Steps in the Release of Sodium Ions by the Na+/K+-ATPase, Nature, 2000, vol. 403, pp. 898-901.

Loew, Confocal Microscopy of Potentiometric Fluorescent Dyes, Methods in Cell Biology, 1993, vol. 38, pp. 195-209.

Rakowski et al., Stoichiometry and Voltage Dependence of the Sodium Pump in Voltage-Clamped, Internally Dialyzed Squid Giant Axon, J. Gen. Physiol., 1989, vol. 93, pp. 903-941.

De Weer et al., Stoichiometry and Voltage Dependence of the Na/K Pump, the Na+,K+-Pump, Part A: Molecular Aspects, 1988, pp. 421-434.

Gadsby et al., Voltage Dependence of Na/K Pump Current in Isolated Heart Cells, Nature, 1985, vol. 315, pp. 63-65.

Gadsby et al., Voltage Dependence of Na/K Pump Current, Current Topics in Membranes and Transport, 1989, vol. 34, pp. 269-288.

Clausen et al., Rapid Activation of the Na+,K+-Pump - Mechanisms and Functional Significance, Biol. Skr. Dan. Vid. Selsk., 1998, vol. 49, pp. 153-158.

Lauger, Na/K ATPase, in Electromagnetic Ion Pumps, 1996, Sinauer Associates, Inc., Sunderland, Massachusetts, pp. 201-204.

Lauger, Electrogenic Ion Pumps, vol. 5, 1991, Sinauer Associates, Inc., Sunderland, Massachusetts, pp. 168 and 213.

* cited by examiner

METHOD OF ELECTROGENICALLY CONTROLLING PUMP MOLECULES

CROSS REFERENCE TO RELATED APPLICATIONS

This application is continuation in part of U.S. patent application Ser. No. 12/231,030 entitled "A Method of Electrogenically Controlling Pump Molecules", filed Aug. 28, 2008, the contents of which are incorporated herein by reference, which is a continuation of International Application, Serial Number PCT/US2007/05200 filed Feb. 28, 2007, the contents of which are herein incorporated by reference, which claims priority to U.S. Provisional Patent Application 60/767,045, entitled, "Electrogenic Pump Molecule Control", filed Feb. 28, 2006, the contents of which applications are herein incorporated by reference.

STATEMENT OF GOVERNMENT INTEREST

This invention was made with Government support under Grant No. NIGM 50785 awarded by the National Institutes of Health and under Grant No. PHY0515787 awarded by the National Science Foundation. The Government has certain rights in the invention.

FIELD OF INVENTION

This invention relates to the control of ion-transporters in a cell membrane. Specifically, this invention relates to the non-invasive control of a plurality of carrier-mediated ion-transporters/ion-exchangers.

BACKGROUND OF THE INVENTION

In living systems, there are many ion-transporters such as electrogenic pump molecules and carrier-mediated ion-exchangers in cell membranes. Functions of these ion-transporters are to maintain the specific ionic concentrations in the cell as well as the ionic concentration gradients across the cell membrane. These ionic concentration gradients result in an electrical potential across the cell membrane. The ionic concentration gradients and the membrane potential constitute electrochemical potential across the cell membrane, which is critical to many cell functions.

This electrochemical potential is the source for the generation and propagation of the action potential for all of the excitable cells, such as nerve cells, skeletal muscle fibers, and cardiac cells. This electrochemical potential also provides energy to many other membrane active-transporters, such as the Na/H exchangers which influence pH value. The ionic concentration gradients also play a significant role in controlling the cell volume and homeostasis. Therefore, maintaining the ionic concentration gradients and the membrane potential is critical to living cells.

The Na/K pump or Na/K ATPase is one of the most prevalent house-keeping proteins and is found within the membrane of almost every cell. It famously extrudes three Na ions out of the cell via the exchange of two K ions and consumption of one ATP in each pumping cycle in order to maintain the ionic concentration gradients and the membrane potential. The energy requirements of the Na/K pumps can constitute 20-80% of the cell's resting metabolic rate depending on the extent of electrical activity of the tissue.

Because stable ionic concentration gradients and membrane potential differences maintained by the Na/K pumps are critical to cell functions and survivability, any functional reduction of the pump molecules will inevitably affect cell functions and may result in cell necrosis and death. There are many situations where the functions of Na/K pumps can be significantly affected. One category of diseases includes those in which there is a lack of ATP molecules. Because a large amount of ATP molecules are used by Na/K pumps, lack of ATP molecules may fail to fuel the pump molecules. Many diseases are in this category, such as cardiac diseases and brain ischemia. Due to lack of blood and oxygen, ATP molecules cannot be effectively generated in the mitochondria to fuel the Na/K pumps. As a result, K ions cannot be sufficiently pumped into the cell and Na ions are accumulated in the cell. The reduced ionic concentration gradients result in membrane potential depolarization. In cardiomyocytes, the ionic concentration gradient reduction and the membrane resting potential depolarization cause many symptoms, such as murmurs, irregular beating, and finally heart failure.

Another example of a lack of ATP molecules failing to fuel the Na/K pump is electrical injury. An intensive electrical shock may generate pore or pore-like structures in a cell membrane, known as electroporation, resulting in leakage of ions and many other biomolecules including ATP from the cell. Due to the lack of ATP molecules to fuel the pump molecules, the ionic concentration gradient cannot be quickly restored. Consequently, the electrically injured cells may be swollen, ruptured, and eventually die.

A second category of diseases in which the Na/K pumps are significantly affected are those in which the density of the Na/K pump molecules in the cell membrane is significantly reduced. In these diseases the residual pump molecules are not competent to maintain the ionic concentration gradients and membrane potential. A short list of these diseases includes myotonic dystrophy, diabetes, cystic fibrosis, central nervous system disorder, McArdle disease, and various aging diseases, such as Alzheimer's disease and Huntington's disease. For example, with regard to Huntington's Disease it has been found that the density of Na/K pump molecules in the brain neurons of those suffering from Huntington's disease may decline to as low as 30%.

Finally, in some diseases the natural mechanisms controlling the functions of Na/K pumps are affected to the point of malfunction of the pump molecules. For example, dysfunction of the pump molecules in the kidneys, peripheral nerves, blood vessels, and muscle fibers in diabetes patients are often due to both metabolic deficiencies and control mechanism defects. Similarly, one of the mechanisms underlying long-term hypertension is related to the level of endogenous ouabain-like compound (EOLC) in the body which is involved in the control of the Na/K pumps. In order to reinstate normal cell functions and reduce the symptoms of disease, effective and efficient control or restoration of the Na/K pump functions has become a central target for treatment.

Many pump molecules and ion-exchangers are sensitive to changes in membrane potential due to the transportation of ions across the cell membrane. The voltage-dependence of Na/K pump current has been widely studied from nerve cells (Rakowski et al, 1989), oocytes (Rakowski et al., 1991), cardiac muscles (Nakao and Gadsby, 1989; Gadsby and Nakao, 1989) and skeletal muscle fibers (Chen and Wu, 2002). The results have shown that Na/K pumps have a sigmoid shaped I-V curve, which exhibits a shallow slope, saturation behavior, and a negative slope when membrane potential is depolarized (Lauger and Apell, 1986; De Weer, et al., 1988; and Rakowski, et al., 1997). These results indicate that the sensitivity of the pump molecules to membrane potential is not particularly high and that the pump current has an upper limit. At normal physiological condition a membrane potential change, by natural mechanisms, can adjust the pump functions to maintain the concentration gradients and membrane potential. However, for many diseases and emergency situations, the natural mechanisms fail to exert a membrane potential change to adjust pump function and membrane potential depolarization results.

In the past few decades, significant efforts have been made to electrically activate the Na/K pumps. The pioneering work by Tsong and Teissie studied the Na and K pumping modes, separately, (Teissie and Tsong, 1980; Serpersu and Tsong, 1983) in red blood cells. They found that a weak oscillating electric field (20V/cm) at 1 MHz can activate the Na pumping mode but failed to facilitate the K pumping mode. Similarly at 1 KHz, the field can activate the K pumping mode but not the Na pumping mode.

Both sinusoidal electric field and random telegraph fluctuating (RTF) electric field have been used as the oscillating field (Xie et al, 1994). A resonance frequency theory was later developed (Markin et al, 1992) to interpret these results. Intrinsic oscillating frequencies may exist for the two pumping modes. When the applied field oscillating frequency resonates with the intrinsic frequency, electric energy will be transduced to the pump molecules to activate the corresponding pumping mode (Tsong and Astumian, 1986, 1987; Markin et. al., 1992; Robertson and Astumian, 1991).

Liu et al. (1990) and Xie et al. (1994) studied the electrical activation of the two transports separately (either Na pumping mode or K pumping mode, not both together). The activation of the whole pumping cycle was not shown. Based on their results of three-orders of difference in the optimal frequencies for the two transports, it is impossible to use one electric field to simultaneously activate both Na and K transports and therefore the whole pumping cycle. In contrast, the present invention activates the whole pumping cycle to accelerate the pumping rate.

Second, in their studies (Liu et al. 1990; Xie et al. 1994) an electric field with a discrete frequency was employed and it was found that there are two separate frequencies that are optimal for either the Na or the K pumping modes. In contrast, the present invention employs an electric field with a sweeping or modulating frequency which is significantly different from a discrete frequency.

In addition, (Liu et al. 1990; and Xie et al, 1994) a field-strength of 20V/cm was used for red blood cells. Based on the 5 μm diameter of the red blood cells, the field-induced membrane potential is about 5 mV. This field-induced membrane potential is significantly smaller than the field-induced membrane potential used in the synchronization modulation method where 30 mV or higher is needed. The significant difference in the field-strength is because underlying mechanisms involved in the two techniques are fundamentally different.

The underlying mechanism of the resonance-frequency-window theory considers the existence of intrinsic frequency windows. When the frequency of an applied oscillating electric recognizes or matches the protein's intrinsic frequency, resonance occurs and the pump molecules can maximally absorb energy from the electric field. In contrast, the underlying mechanism of the present invention is that the pump's turnover rate is entrainable by a specially designed oscillating electric field. The concept of intrinsic frequencies is not included in the synchronization modulation method. When a well designed oscillating electric field with a frequency comparable to the pump's physiological turnover rate is applied to the cells, the Na-extrusion and K-influx is eventually trapped into positive and negative half-cycles, respectively. All the individual pumps operate at the same pumping pace as the oscillating electric field, i.e. the pumping rate is synchronized to the field frequency. By carefully maintaining the pump synchronization and gradually increasing (or decreasing) the field frequency, the pumping rate can be progressively re-synchronized to new frequencies, up to a defined value.

The outputs of the resonance-frequency-window theory also differ dramatically from those of the synchronization modulation method. In the resonance-frequency-window theory, when responding to an electric field with an optimal frequency, the corresponding pumping mode will be activated. The pumping mode cannot be deactivated or controlled to a defined value. In contrast, the synchronization modulation method allows not only the activation or deactivation of the pumping rate but also can control the pumping mode to a defined pumping rate. The resonance-frequency-window theory is only a simple phenomenon of energy absorption while the synchronization modulation method is a procedure of dynamic entrainment of the pump molecules.

A second theory has been proposed for the activation of pump molecules. This theory is known as the excitation-stimulation theory. Clausen, in an excellent review [Clausen, T., 2003, Na/K pump regulation and skeletal muscle contractility, *Physiological Review,* 83:1269-1324], has summarized the underlying mechanisms involved in excitation-stimulation-induced activation of the Na/K pumps. Activation of the Na/K pumps elicited by excitation-stimulation is most likely to reflect a rapid, but slowly reversible increase in the affinity of the Na/K pump for intracellular Na ions, possibly elicited by depolarization during the action potentials. This would allow for a more efficient clearance of Na from the cytoplasm and K from the extracellular phase. Another possible mechanism is due to the excitation-induced leakage of Na and K ions which increase the availability of ions to bind with the pump molecules [Clausen, T., and Nielsen, O. B., 1998, Rapid activation for the Na/K pump: mechanisms and functional significance, Bio. Skr. Dan. Vid. Selsk., 49:153-158].

Clausen et al showed that excitation-stimulation can activate the Na/K pump functions in skeletal muscles (1998 and 2003), where the stimulation opens the Na and K channels and therefore increases the ion-availability and their binding affinity to the pumps. This is actually the natural mechanism in adjusting the pumping functions to maintain the physiological ionic concentration and the membrane potential. No electrical energy is involved in the pump molecules. Excitation-stimulation is successful in the natural physiological situation but not in the extraordinary situation such as in disease or injury.

The electric field used in the excitation-stimulation method neither directly influences the pump molecules nor delivers electrical energy to the pumps. Because the channel currents are much larger than the pump currents, skeletal muscles still undergo a net loss of K ions and a net gain of Na ions (Sejersted et al., 2000, Kiernan et al, 2004, Moldovan and Krarup, 2006). The increased intra-neuronal Na ions may lead to reversal of the Na/Ca exchanger (Tatsumi and Katayama, 1995) and trigger the destruction of peripheral axons (Smith and Hall, 2001; Waxman, 2005). Therefore, in spite of its activation effect, the excitation-stimulation method has negative functional consequences. In contrast, the synchronization modulation method directly affects the pump molecules by precisely providing electric energy to the Na- and K-transports in the positive and negative half-cycles, respectively.

Other models to explain the underlying mechanisms have been proposed including a Brownian motion model (Astumian, 1997, Tsong, 2002, 2003) and a recent adiabatic pump model (Astumian, 2003). However, most of these studies are mainly hypothesis or theoretical analysis. As discussed above, the synchronization modulation method is significantly different from both the resonance-frequency-windows theory and the excitation-stimulation method in many aspects including the basic concept and underlying mechanisms, the approach, and the output.

To date, there is no practical technique available to non-invasively and effectively activate the pumping cycle or accelerate the pumping rate of the Na/K pumps or other carrier-mediated ion transporters. This may be due to the pump molecules not being particularly sensitive to the membrane potential as evidenced by a sigmoidal shaped I-V curve. It may also be due to the difficulty in electrically increasing the pump currents by simply depolarizing the membrane potential. Thus, there is needed in the art a mechanism by which to activate the entire pumping cycle (both Na and K transports) and accelerate or decelerate the pumping rates of the Na/K pumps or other carrier-mediated ion transporters.

The present invention discloses a method of controlling the entire operating (pumping) cycle of a plurality of carrier-mediated ion transporters. Controlling the ion transporters is accomplished by synchronizing the turnover rate of the individual carrier-mediated ion transporters through the application of a specially designed oscillating electric field at a frequency initially comparable to the natural turnover rate of the ion transporter. After the turnover rates of the individual ion transporters are synchronized, the turnover rates are modulated by gradually adjusting the synchronization frequency in order to control their running cycle. The synchronization modulation method of the present invention can effectively control the entire pumping cycle of a plurality of ion-transporters.

SUMMARY OF THE INVENTION

The method of synchronization modulation consists of two main steps: the synchronization of individual ion transporters in which all of the ion transporters are forced to operate at the same pumping rate and pumping phase and the incremental modulation of the pumping rate to entrain the transporters' turnover rate through either increasing or decreasing the rate.

In the synchronization step, a specially designed oscillating field is applied to the plurality of ion transporters and the pumping rates of the individual ion transporters are synchronized to the oscillating electric field frequency. This synchronizing oscillating electric field has been designed in waveform, magnitude, and frequency based on the ion-transporter's physiological parameters.

These parameters include: the initial oscillating frequency must be comparable to the natural turnover rate of ion transporters; the waveform can be sinusoidal, various pulses, or other oscillating waveforms with a square-pulse waveform being preferred; the waveform can be either asymmetric or symmetric with a symmetric waveform being preferred; and the magnitude of the oscillating field should be restricted to a value where the field-induced membrane potential falls within the physiological range.

An embodiment of the invention is a method of controlling the cycle of a plurality of carrier-mediated ion transporters by applying an oscillating electric field at a predetermined synchronization frequency that is substantially equal to the ion transporters initial natural turnover rate in order to synchronize the individual ion transporters. After the individual ion transporters are synchronized, the synchronization frequency is incrementally adjusted (either increased or decreased) to control the cycle. The ion-transporters should be sensitive to membrane potential and have an ion-transport step that is the rate-limiting step to their respective reaction.

In this embodiment, the synchronization frequency of the oscillating electric field is able to be changed through changing oscillating cycle duration by applying either continuous, incremental, small changes in the cycles of about 1% or less of the cycle duration or by applying large incremental changes in repeating cycles of between about 3% and about 5% of the cycle duration.

In this embodiment, the maximum frequency incremental change is between half of the previous frequency and double the previous frequency. The maximum incremental change in the oscillating cycle is between about half of the previous cycle duration and double the previous cycle duration.

In addition to the turnover rate being modulated to accelerate when the synchronization frequency is gradually increased, the turnover rate can also be reverse modulated when the synchronization frequency is gradually reduced.

In another embodiment of the present invention, a method of controlling the cycle of a plurality of Na/K pump molecules is presented. Controlling the Na/K pump molecules is accomplished through the application of an oscillating electric field at a predetermined frequency that is substantially equal to the pump molecules' initial turnover rate after which the synchronization frequency is incrementally adjusted to control the cycle.

In this embodiment, the magnitude of the oscillating electric field is restricted to a magnitude that allows the field-induced membrane potential to fall within the physiological range.

The synchronization frequency of the oscillating electric field can be changed by changing pulse duration. The pulse duration can be changed through the application of small changes in continuous consecutive pulses of less than about 1% of the pulse duration or large incremental changes in repeating pulses of between about 3% and about 5% of the pulse duration.

The maximum frequency incremental change should be between half and double the previous frequency. The maximum pulse duration change should be between half and double the previous pulse duration.

The synchronization frequency can be increased or decreased in order to modulate the turnover rate to accelerate (forward modulation) or decelerate (reverse modulation).

In a further embodiment, a method of treating a disease in a subject characterized by a deregulation in Na/K pump molecule function is presented. The disease is treated through controlling the Na/K pump molecules which is accomplished through the application of an oscillating electric field at a predetermined frequency that is substantially equal to the pump molecules' initial turnover rate after which the synchronization frequency is incrementally adjusted to control the cycle.

Diseases that can be treated by the synchronization modulation method include, for example: myotonic dystrophy, diabetes, cystic fibrosis, central nervous system disorders, McArdle disease, Alzheimer's disease, Huntington's disease, hypertension, brain ischemia, cardiac diseases, and electrical injury.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
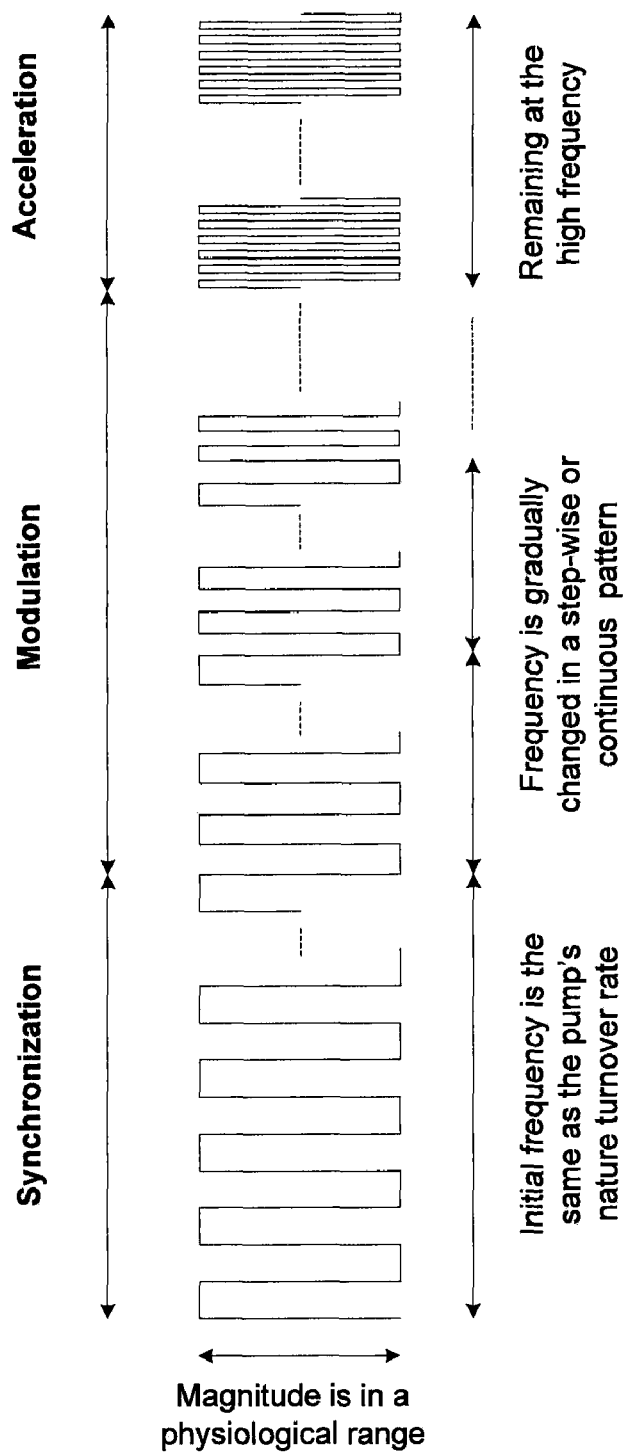
FIG. 1 is an image depicting the synchronization modulation method. The oscillating electric field has an initial oscillating frequency comparable to the pumps natural turnover rates. After a certain number of oscillating pulses, the field gradually increases its frequency or decreases the pulse duration in a step-wise pattern. Then by gradually increasing the oscillating frequency or decreasing the pulse duration, the pumps are modulated to pump at the same rate.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used herein, the terms "ion-transporter", "ion pump", "ion-exchanger", and "pump molecule" are used interchangeably to denote the movement of ions across a plasma membrane. The movement of ions can be through active or passive transport. In addition, the ion-transporters can be electrogenic or non-electrogenic. Na/K pumps are used as an example of one type of ion transporter that can be entrained by the present invention however; the invention is applicable to any ion transporter.

As used herein, the term "substantially equal" refers to any frequency that is within the range of frequencies naturally displayed by the ion transporters natural turnover rate in the physiological state. For example, the average natural turnover rate for Na/K pumps/ion transporters is 50 Hz, however individual Na/K pumps/ion transporters may operate at 60 Hz or 40 Hz. The term "substantially equal" is meant to cover all frequencies of natural turnover rates that could be naturally displayed by the ion transporters in their physiological state. This range of frequencies for the ion transporters natural turnover rate in the physiological state is well known to those of ordinary skill in the art.

The term "step-wise" as used herein, refers to incremental changes. The term "step-wise" is used herein synonymously with the terms "incremental change". These incremental changes can be made to the oscillating cycle duration, pulse duration or the frequency. These incremental changes can be increased (additive—for forward modulation) or decreased (reduced for reverse modulation).

Many pumps, or carrier-mediated ion transporters such as the Na/K pump, move one kind of ion out of cells by exchanging for another kind of ion. Some ion-exchangers, such as Na/K ATPase, consume ATP while others do not. Ion exchangers can be electrogenic or non-electrogenic. Microscopically, for each electrogenic pump or ion-exchanger, there should be two components of the currents in each running loop, an outward current representing the outward ion transport and an inward current representing the inward transport. However, because of environmental differences, individual ion-exchangers may not have the same turnover rate and may run at random phases due to structural independence.

The ability to physically manipulate the functions of membrane proteins, especially the active transporters, is a pursuit that has interested and challenged many researchers. The inventor has developed a method using a specially designed oscillating electric field to effectively synchronize and control the pump functions of a plurality of pump molecules or ion-transporters. The new method of synchronization modulation provides a novel approach to significantly activate ion-transporters such as the Na/K pumps by first synchronizing all the ion-transporters and then gradually modulating their pumping rate to a defined value. The pump synchronization modulation method can be viewed as a dynamic entrainment procedure that was designed to control a plurality of ion-transporters.

The inventor has used the Na/K pump as an example in studying synchronization modulation of a group of carrier-mediated ion transporters in a physiological operating mode by applying the concept of an electronic synchrotron to the biological system. Synchronization of the pump molecules is more complicated than the synchronization of an electronic beam. In a synchrotron, the acceleration electric field can be applied specifically to the pathway of the electronic beam. Practically, it is impossible to apply an electric field to specifically influence one transport without affecting the other. Any applied electric field will inevitably affect the two transports oppositely. The method of synchronization modulation developed by the inventor uses a specially designed oscillating electric field to synchronize and modulate the pumping rates of the ion-transporters thus allowing effective control of the entire cycle.

The mechanism involved in the synchronization of carrier-mediated ion-exchangers, by using the Na/K pump as an example, was investigated (Chen, W., Synchronization of carrier-mediated pump molecules by an oscillating electric field: Theory, *Journal of Physical Chemistry B,* 112 (32), 10064-70, 2008). First, the inventor studied the underlying mechanisms involved in the sigmoidal shaped I-V curve of the pump molecules (Chen, W., Voltage dependence of the carrier-mediated ion transport. *Physical review.* E, Statistical, nonlinear, and soft matter physics February; 73 (2 Pt 1): 021902-1-7. 2006) and found that because the pump molecule transports Na and K ions in opposite directions, the two transports have reverse voltage-dependence. Any membrane potential change, either depolarization or hyperpolarization, cannot facilitate both ion-transports but rather can only facilitate one transport and inevitably hinder the other. Consequently, the whole pumping cycle cannot be significantly accelerated.

At the membrane resting potential, the K-transport is faster than the Na-transport resulting in the turnover rate of the Na/K pump being mainly determined by the Na transport. When the membrane potential is depolarized, it facilitates the Na-transport but hinders the K-transport. Because the Na-transport is the rate-limiting transport in the pumping loop, facilitating the Na-transport accelerates the pumping cycle and increases the pump currents resulting in the I-V curve showing a positive slope. Up to a certain membrane potential, the time-course of K-transport becomes comparable to that of Na-transport, and therefore, a membrane potential depolarization can no longer increase the pumping rate. This is represented as the plateau in the pump I-V curve. When the membrane potential is further depolarized, the K-transport becomes the rate-limiting transport. Hindering the K-transport will slow down the pumping cycle and decrease the pump currents, showing the negative slope of the I-V curve (Chen W, Voltage dependence of the carrier-mediated ion transport. *Physical review.* E, Statistical, nonlinear, and soft matter physics February; 73 (2 Pt 1):021902-1-7. 2006).

In the development of the synchronization modulation method to control the pump cycle, it was noted that the two ion-transports do not occur simultaneously but rather occur in a sequential pattern. The pump molecule extrudes Na ions and subsequently pumps in K ions. There are two different time-windows that allow treatment of the two transports separately. Application of a special oscillating electric field where the duration of the positive and negative half-cycles exactly matches the time-courses of the Na- and K-transports, respectively, so that the pump extrudes Na ions during the positive half-cycle and then pumps in K ions in the negative half-cycle has been shown to be effective. During the positive half-cycle the electric field depolarizes the membrane potential thus reducing the energy barrier of the Na-transport and activating the Na-transport. Similarly, during the negative half-cycle, the field hyperpolarizes the membrane potential thus reducing the K-transport energy barrier and facilitating the K-transport. The electric field at the two half-cycles alternately facilitates the two transports and therefore, significantly accelerates the pumping rate. Use of this specially designed oscillating electric field allows the Na/K pump currents to significantly increase thus showing an exponential-like I-V curve without saturation.

However, because there are many pump molecules in a cell membrane each of which has a different pumping rate and random pumping pace, it is impossible to use a single oscillating electric field to match all the pumping cycles of individual pumps. In order to control the entire operating cycle of a plurality of carrier-mediated ion transporters, it is necessary to first synchronize all of the pumps to operate at the same pumping rate and pumping phase. Once the pumps are synchronized so that all the pumps extrude Na ions during the positive half-cycles and pump in K ions during the negative half-cycles, both the transports are facilitated and the pumping rate is increased. In order for the two half-cycles to match the two transports, the field frequency has to be increased correspondingly to exactly follow the changes in the pumping rate.

The method of synchronization modulation consists of two steps. The first step is synchronization of individual pump molecules in which all of the pump molecules are forced to operate at the same pumping rate and pumping phase. For the Na/K pump molecules this is defined as synchronizing the pumping rates of individual pump molecules to the oscillating frequency and extruding Na ions during the positive half-cycle and then pumping in K ions during the negative half-cycle. The inventor has designed the synchronization oscillating electric field in waveform, magnitude, and frequency based on the pump's physiological parameters. This specially designed electric field has been used to synchronize the Na/K pumps so that they all extrude Na-ions during the positive half-cycle, and then pump in K-ions in the negative half-cycle. The parameters of the oscillating electric field are as follows:

First, the initial oscillating frequency must be comparable to the natural turnover rates of the pump molecules/carrier-mediated ion-transporters. For the Na/K pumps, the natural turnover rates have been shown to be around 50 Hz. For different pumps or ion-exchangers, the natural turnover rate may differ significantly.

Second, the waveform of the oscillating electric field can be sinusoidal form, various pulses, or other oscillating waveforms. Based on the theoretical analysis and experimental results, a squared-pulse waveform is more efficient than other waveforms.

Third, the waveform of the oscillating electric field can be asymmetric so that the two half-cycles match the time-courses of the Na- and K-transports, respectively. Alternatively, the oscillating electric field can have a symmetric waveform showing the same duration for the two half-cycles. Both the symmetric and asymmetric waveforms can be used to synchronize the pump molecules as long as the field-strength is well designed. Considering biological and clinical applications to intact cells, tissues, and organs, the symmetric waveform is preferred. For most cells which are not polarized, or where the pump molecules are relatively evenly distributed in the two opposite hemispheres, the symmetric oscillating electric field can effectively synchronize the pump molecules in both hemispheres.

Fourth, the magnitude of the oscillating electric field should be restricted so that the field-induced membrane potential falls within the physiological range. In this range, the higher the magnitude of the oscillating electric field, the easier the pump molecules can be synchronized. Even if the field-strength is not high, the electric field will tend to synchronize the pumping rate. However, the pump synchronization may not be stable and the pumps may jump back and forth between synchronized and unsynchronized conditions. For the best results, the electric field at the positive half-cycle, which depolarizes the cell membrane and facilitates the ion-extrusion, should block the transport that pumps cations into the cell, the ion-intrusion. For example, it has been shown that if the field-induced membrane potential alternates the membrane potential from −50 mV to −130 mV (at a membrane resting potential of −90 mV), the pump synchronization is very stable because the energy needed for the pump to extrude 3 Na ions in the negative half-pulse exceeds the metabolic energy from a single ATP hydrolysis. Thus, the Na-extrusion is fully inhibited in the negative half-cycle.

The upper limit of the field-strength should be restricted so that the field-induced membrane potential, including the resting potential, should be less than −200 mV, in order to avoid damaging the cell membrane. The inventor has shown that the threshold of the membrane potential to electroporate the cell membrane is between 250 to 300 mV (Chen, W. and Lee, R. C., An improved double vaseline gap voltage clamp to study electroporated skeletal muscle fibers. *Biophysical Journal.* 66:700-709, 1994). For the above mentioned oscillating electric field 50 pulses is enough to synchronize the Na/K pumps.

The patterns of the synchronized pump currents differ significantly from that of the randomly paced pumps. Microscopically, current generated by each Na/K pump should include two alternatively appearing components: outward Na and inward K pump current. However, the inward K pump current cannot be distinguished from the outward current for the randomly paced pumps. In all currently available electrical measurements only a small net outward pump current could be observed mainly responding to a positive pulse that depolarizes the membrane potential. Due to the random pumping paces, the outward Na currents and inward K currents from individual pumps are combined and cancel each other out thus resulting in a small net outward current. In contrast, when the pumps are synchronized, all individual pumps extrude Na-ions during the positive half-cycle and then pump in K-ions during the negative half-cycle. The outward Na currents and inward K currents are separated corresponding to the positive and negative half cycles, respectively.

The characteristics of the synchronized Na/K pump currents include (Chen, W., Zhang, Z. S., and Huang, F., Synchronization of the Na/K pumps by an oscillating electric field, *Journal of Bioenergetics and Biomembrane*, August 2. [Epub ahead of print], 2008): (1) a distinguishable inward pump current that is revealed alternating with the outward current; (2) a much larger magnitude of the outward pump currents as compared to the randomly paced pump currents; (3) a magnitude ratio of the outward over inward pump currents that is close to 3:2, which reflects the pumps' stoichiometric number; (4) a pumping rate that is restricted to the field frequency, and a pump current that remains unchanged regardless of an increase in the field-strength because the stoichiometric numbers of the pump molecules do not change in a wide range of the membrane potentials (Rakowski, et al., 1989; De Weer, et al., 1988); and (5) synchronized pump molecules that remain synchronized for another half-cycle after removal of the field.

The second step of the synchronization modulation method is the modulation of the pumping rate. The goal of this step is to entrain the pumps' turnover rate through either increasing or decreasing the rate. As long as the pump molecules are synchronized to the oscillating electric field so that the pumping rates are restricted to the field frequency, a slight change in the field frequency will quickly re-synchronize the pumps to the new frequency. The frequency can subsequently be changed again to increase or decrease the turnover rate. The pump molecules will remain synchronized to the oscillating electric field as long as the frequency change, regardless of whether the change increases or decreases the rate, is small enough. As a result, the pumping rates will be progressively modulated (accelerated or decelerated) to a defined value. By gradually increasing or decreasing the synchronization frequency, and carefully keeping all the individual pumps in synchronization with the field frequency, the pumping rate can be progressively modulated to higher or lower pumping rates.

The inventor has shown that once the pump molecules are synchronized to the applied oscillating electric field, a small change in the field frequency will not affect the pump synchronization. All of the pumps will remain extruding Na ions and pumping in K ions in the positive and negative half-cycles, respectively since the electric field at the positive half-cycle always reduces the energy barrier for the Na-extrusion but increases the barrier for the K-influx. In a well designed waveform and magnitude, the Na-extrusion will be trapped in the positive half-cycles and the K-influx will be excluded. Similarly, the K-influx will be trapped into the negative half-cycle. Therefore, a small change in the synchronization frequency will not affect the pump synchronization status and can quickly re-synchronize the pumps to the new frequency.

There are two methods to change the field oscillating frequency. The first method is continuous change of the field frequency in which each consecutive oscillating pulse has a small change in the pulse duration. If continuous change is used, the changes must be made in small increments, preferably of 1% or less of the pulse duration. Alternatively, the frequency change can be step-wise in which the change in pulse duration is made in slightly larger increments as compared to continuous change however, for each change, the field repeats the same frequency oscillation for a number of cycles. The inventor has discovered that a 3-5% change in the pulse-duration or oscillating frequency followed by a 10 pulse repeat is able to effectively modulate the pumping rate of Na/K pumps. In general, the larger the frequency step-change, the more repeating-pulses are needed to insure re-synchronization of the pumps to the new frequency. Also, the higher the pulse magnitude, the larger the frequency step-change can be used to re-synchronize the pump molecules.

The inventor has shown that if the oscillating field frequency approaches either double or half of the previous frequency, or the pulse-duration approaches either double or half the previous duration, the electric field can no longer re-synchronize the pump molecules to the new frequency regardless of the pulse magnitude. It is necessary to point out that once a pump molecule is unsynchronized and returns to a random pumping rate, it is difficult to resynchronize it. This is especially true when the pumping rate has been modulated far away from the natural turnover rate. Therefore, it is critical to make small incremental changes in the field frequency to insure re-synchronization of most of the pump molecules.

In addition to the field-strength, the range of the step-change in the frequency modulation may depend on the kind of pump molecules or ion-exchangers. For the Na/K pumps, the field-parameters mentioned above are sufficient to resynchronize the pumps to the new frequency, and therefore, accelerate the pumping rates. For other pump molecules, the actual frequency step-change may differ, however a small change is always necessary in order to modulate the ion-exchangers. The time needed to modulate the turnover rate is trivial. For example, modulation of the Na/K pumps from 50 Hz to 500 Hz with a frequency step-change of 3% and 10 repeating pulses takes less than one minute.

For each magnitude of the oscillating electric field, there is a maximum pump turnover rate that can be modulated by a given field-strength. For example, in the Na/K pumps, an oscillating electric field-induced membrane potential having a magnitude of 60 mV can modulate the pumping rate up to ten-fold from a physiological value of 50 Hz thus reaching a turnover rate of 500 Hz. The higher the field-strength, the higher the pumping rate the electric field can modulate to. In order to activate the pumping rate to higher value, the magnitude must be correspondingly increased.

Alternatively, the pumping rate can be reverse modulated to a lower value. When the synchronization frequency is gradually decreased following the above criterion, the pumps' turnover rate can be gradually reduced to a defined value. Using the above parameters, the pumping rate of the Na/K pumps can be reduced ten-fold, to 5 Hz. Because the pulse-duration becomes longer, the time needed for the reverse modulation is longer than that needed for the forward modulation.

The pump synchronization modulation method is not restricted to any specific pump molecules. Na/K pump molecules were used only as an example of the method. The synchronization modulation method, in general, can be used for all ion transporters, especially for the ion-exchangers, regardless of consumption of ATP molecules. The detailed parameters of the oscillating electric field may be adjusted to effectively apply to each specific transporter. However, the underlying methods remain the same: the initial synchronization frequency must be comparable to the natural turnover rate of the transporters; the smaller the step-change in frequency modulation, the less repeating pulses are needed; the upper and lower limits of the frequency step-change are double and half, respectively; and the maximal or minimal turnover rate to which the transporters can be modulated depends on the field-strength.

FIG. 1 is an illustration depicting the synchronization modulation method. The first part is the synchronization step which consists of 100 oscillating pulses having an oscillating frequency of 50 Hz or a half-pulse duration of 10 ms which is comparable to the Na/K pumps turnover rates. Then, the oscillating frequency is gradually increased or the half-pulse duration gradually decreased in a step-wise pattern, which constitutes the second part, modulation. In each step, the half-pulse duration is reduced for 5% and repeated for 10 pulses. Once reaching the final half-pulse duration of 1 ms or the final oscillating frequency of 500 Hz, the electric field will retain the frequency until removal of the field.

The underlying mechanisms involved in the synchronization modulation of pump molecules or ion-exchangers are: design of an oscillating electric field that can alternately change the energy differences in the two ion-transports; examination of the effects of the electric field on the two consecutive ion transports; examination of the characteristics of synchronized pump currents; and examination of the possible I-V curve of the synchronized pump molecules as a function of the synchronization modulation electric field. The Na/K pump is used throughout as an example of a pump molecule that can be controlled by the synchronization modulation method.

Design of the Oscillating Field

In order to understand the background of the Na/K pump molecules, it is necessary to point out two facts. First, the Na/K pump extrudes 3 Na ions and then pumps in 2 K ions. The two ion-transports occur sequentially in the pumping loop. Therefore, there is a time-window to specifically treat each ion-transport. Second, because the Na and K ions are moving in opposite directions, the two ion-transports have reverse voltage-dependence. Therefore, an oscillating electric field can be designed to distinguishably influence the two transports separately.

The energy differences in the two ion-transports can be easily calculated. For skeletal muscle fibers, the intra- and extra-cellular Na concentrations are about 4.5 mM and 120 mM, respectively (Hille, 2003). The chemical energy difference can be expressed as the equilibrium potential of 60 mV based on the Nernst-equation (Hille 2003). Starting from a simple oscillating electric field, a symmetric pulsed oscillating waveform alternates the membrane potential from −50 to −130 mV based on the membrane resting potential of −90 mV. Assuming that the Na-extrusion falls into the negative half-pulse, extrusion of a single Na ion out of the cell requires (60+130)=190 meV of energy. In order to extrude 3 Na ions, 570 meV is needed, which is higher than the membrane resting potential of 3(60+90)=450 meV. Therefore, the Na-extrusion will be hindered during the negative half-pulse. This has been termed a hindering half-pulse.

Figure 2:
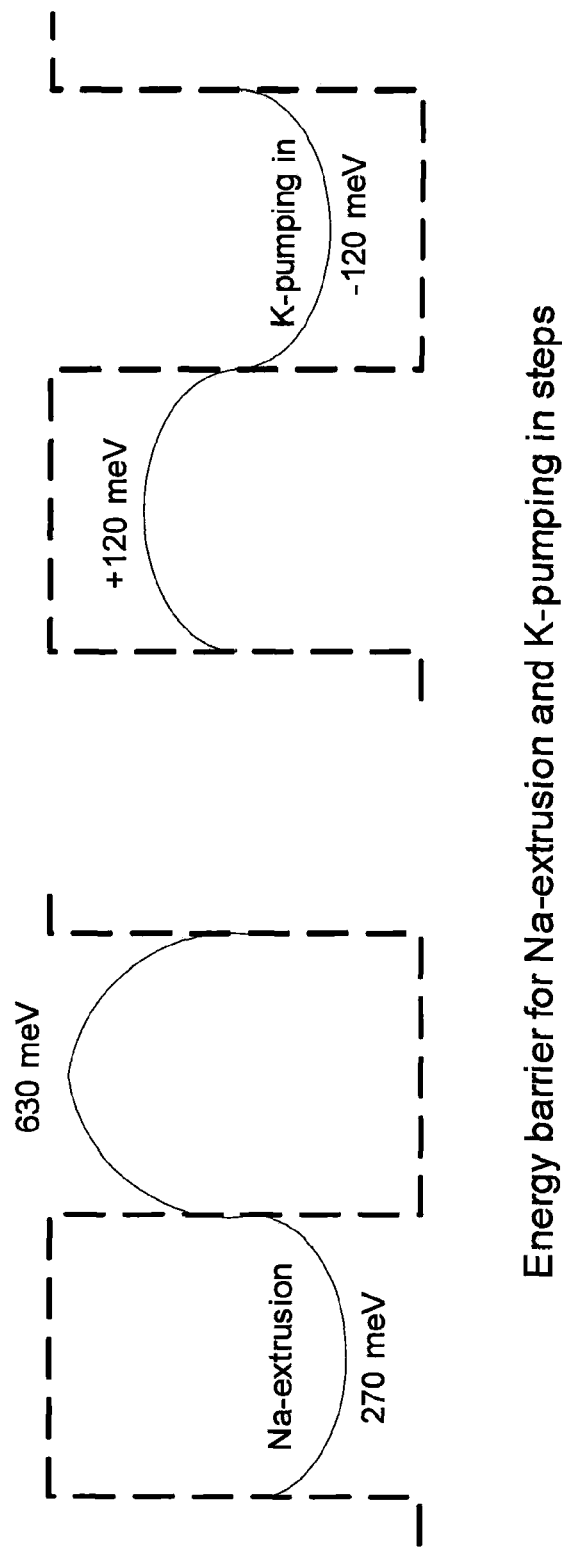
FIG. 2 is an image depicting the schematics of energy barriers and energy traps for Na extrusion and K influx in positive and negative half-pulses.

If the Na-extrusion falls into the positive half-pulse of −50 mV, the energy difference for extruding 3 Na ions is significantly reduced to 3(60+50)=330 mV which is lower than that at the membrane resting potential as shown in FIG. 2. Consequently, Na-extrusion will be facilitated during this period, which has been termed a facilitating half-pulse.

Similarly, based on the intra- and extra-cellular K ion concentrations of 115 and 5 mM, respectively (Hille, 2003), the chemical potential can be expressed as the K equilibrium potential of 90 mV (Hille, 2003). The energy needed to pump in 2 K ions during the positive half-pulse is 2(90−50)=80 meV, whereas during the negative half-pulse it is significantly reduced to a negative value of 2(90−130)=−80 meV (FIG. 2). In comparison with the energy difference at the membrane resting potential of 2(90−90)=0 meV, the K-influx step will be facilitated during the negative half-pulse and hindered during the positive half-pulse.

Effects of the Oscillating Electric Field on the Two Consecutive Ion Transports

Applying the oscillating electric field to a group of pump molecules with different pumping rates and random pumping phases gives three possible cases:

In Case 1, the initial pumping rate is far higher than the field oscillating frequency, or $d_o < T/2$, where d is the time-interval between the two ion-transports in the pumping loop and $d_o$ is the initial time-interval without the field application, and T is the half-pulse duration of the oscillating electric field. In this case, both transports can fall into either a single pulse or two consecutive pulses as the pulse changes its polarity.

In Case 2, the initial pumping rate is comparable to the field frequency, $T/2 < d_o < 2T$. The two transports are most likely falling into two half-pulses, alternately. There are two situations: either both transports are hindered or both transports are facilitated.

In Case 3 the initial pumping rate is far lower than the field frequency, $d_o > 2T$.

Figure 3:
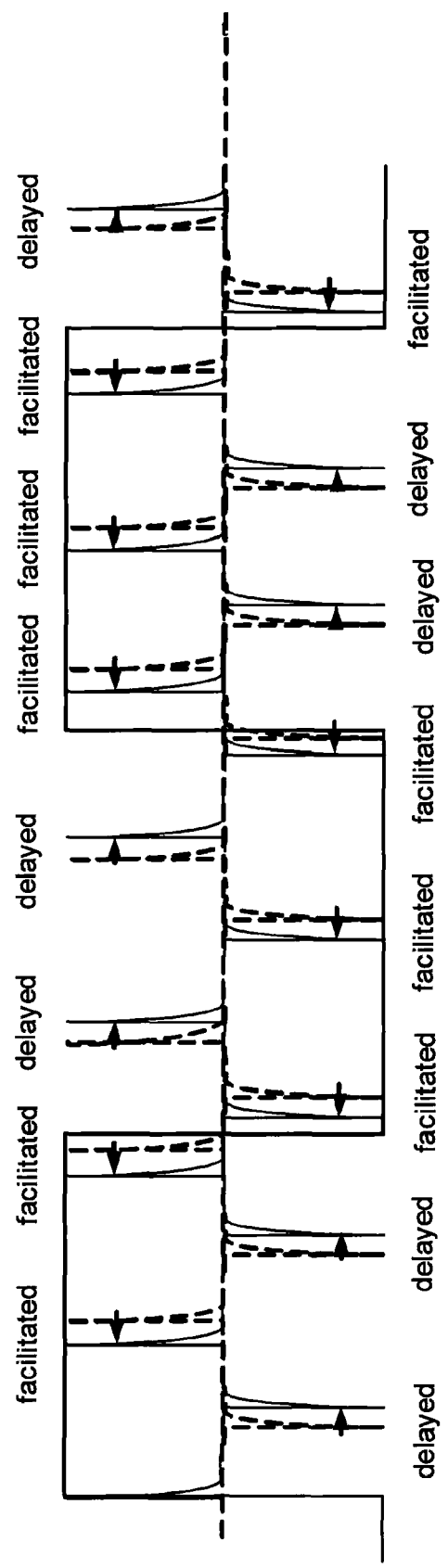
FIG. 3 is an image depicting the scenario when the pumping rate is much smaller than the field frequency (d<<T) and both transports fall into either a positive or a negative half-pulse. For example, in the Na/K pump molecule, Na extrusion falls into the positive half-pulse and K influx falls into the negative half-pulse. The time interval d does not change significantly. The currents shown by the dotted line represent the assumed position of the pump currents without the electric field, and the currents shown by the solid line represent pump currents after field-induced inhibition or facilitation. For simplicity, the field-induced facilitation will not be considered in other figures.

Case 1 is depicted in FIG. 3 in which the initial pumping rate is far higher than the field oscillating frequency, $d_o < T/2$. When both transports fall into the same half-pulse, the electric field facilitates one transport and hinders the other (FIG. 3). If it is a positive half-cycle which is equivalent to a dc depolarization pulse, the total energy needed for the two ion-transports is about 330+80=410 meV, which is smaller than that at the membrane resting potential of 450+0=450 meV. The pumping rate is accelerated but not significantly because only is the Na-extrusion is facilitated while the K-influx is hindered. If it is a negative half-cycle, which is similar to a dc hyperpolarization pulse, the energy needed for the entire pumping loop is 570−80=490 meV, which is a little higher than at the membrane resting potential. The pumping rate is reduced because the Na-extrusion is hindered even though the K-influx is facilitated. The Na-extrusion is generally slower than the K intrusion.

Because the electric field always facilitates one transport and hinders the other, the field-effects on the two transports cannot be accumulated to affect the whole pumping rate. Therefore, only the first pair of transports is affected resulting in a change in the time-interval, d, so that the pumping rate quickly reaches a steady-state. This can be seen from the experimental results using a single pulse to study the Na/K pumps. The elicited pump currents show a quick response to the rising phase of the pulse.

When the pulse changes its polarity, the Na-extrusion may fall into a negative half-pulse and the K-influx into a positive half-pulse which results in both transports being hindered. The total energy needed for a loop is 570+80=650 meV which allows the time-interval d to increase more significantly than in the above situation where both transports fall into the same half-pulse. However, this situation can only happen when the pulse changes its polarity, and then quickly returns to the above situation where both transports fall into the same half-pulse (FIG. 3). It has been shown that neither the Na nor K transient current represents a rate-limiting step of the loop (Lauger, 1991). Since neither transient current represents a rate-limiting step in the loop, hindering the two transports once cannot significantly alter the pumping rate.

Alternatively, the Na-extrusion may fall into a positive half-pulse and K-influx into a negative half-pulse when the pulse changes its polarity which causes both transports to be facilitated. The energy needed for a loop is 330−80=250 meV, which is much lower than that needed at the membrane resting potential. The time-interval d is decreased. Again, due to not being a rate-limiting step in the loop, one time facilitation in two ion-transports will not significantly accelerate the pumping rate.

In summary for Case 1, because the initial pumping rate is far higher than the field oscillation frequency the field always affects the two transports oppositely, thus the field-effects cannot be accumulated. The pump rate quickly changes in response to the two half-cycles of the oscillating electric field, and continually repeats.

In Case 2, the pumping rate is comparable to the field oscillating frequency, or $T/2 < d_o < 2T$. In contrast to Case 1 where the pumping rate quickly reaches two steady-states alternately in response to two half-pulses, the field effects on the pumping loop are accumulated if the two transports repeatedly fall into either hindering or facilitating half-pulses. Facilitation (hindering) on the first ion-transport increases (decreases) its products which go through the intermediate steps and eventually increases (decreases) the reactants of the second transport. This reactant increase (decrease) and the electrical facilitation (hindering) on the second transport will in turn further facilitate (hinder) the first transport. Consequently, the change in the time-interval, d, will be accumulated in the succeeding half-pulses, and therefore the pumping rate is changed.

In this situation, the phase-difference, t, is defined as the time-interval between the transport and the rising phase of the half-pulse in which the transport falls. The initial phase-difference is designated $t_o$. Because of the difference in the pumping rate and the oscillating electric field, this phase-difference will be accumulated in the succeeding half-pulses.

For the first situation in which both transports alternately fall into the hindering half-pulses repeatedly, each half-pulse will hinder the corresponding transport and therefore increase the time-interval d with respect to the previous transport. As the field oscillates, the time-interval d becomes larger and larger. For simplicity, assume that the hindering effects on both transports are very similar, each half-pulse increasing the time-interval d by a factor of a. The time-interval d will be gradually increased in the succeeding half-pulses, which will significantly affect the phase-difference.

When the initial time-interval $d_o$ between the two transports is a little shorter than the half-pulse duration, $T/2 < d_o < T$, the phase-difference $t_n$ in the succeeding $n^{th}$ half-pulses can be expressed as:

$$\begin{aligned}
t_1 &= t_o - (T - d_1) \\
&= t_o - [T - (d_o + a)] \\
&= t_o - (T - d_o) + a
\end{aligned} \quad (1)$$

$$\begin{aligned}
t_2 &= t_1 - (T - d_2) \\
&= t_1 - [T - (d_o + 2a)] \\
&= t_o - [T - (d_o + a)] - [T - (d_o + 2a)] \\
&= t_o - 2(T - d_o) + 3a
\end{aligned}$$

$$\begin{aligned}
t_3 &= t_2 - (T - d_3) \\
&= t_2 - [T - (d_o + 3a)] \\
&= t_o - 2(T - d_o) + 3a - [T - (d_o + 3a)] \\
&= t_o - 3(T - d_o) + 6a
\end{aligned}$$

$$\ldots$$

$$t_n = t_o - n(T - d_o) + a\sum_{i=1}^{n} i \quad n = 0, 1, 2, \ldots$$

Here the second term represents a down-accumulation of the phase-difference due to initially $d_o<T$, and the third term represents the field-hindering effects. The second and third terms have opposite signs. The second term increases linearly with n while the third term increases by the much faster rate of n(n+1)/2. Consequently, when the number n increases, the phase-difference, $t_n$ is eventually accumulated up to be larger than the half-pulse duration, T, or the transport falls into the following facilitating half-pulses.

When the initial time-interval $d_o$ is a little longer than the half-pulse duration, $T<d_o<2T$, the phase-difference up-accumulation is even faster which is expressed as:

$$t_1 = t_o + (d_1 - T) \quad (2)$$
$$= t_o + [(d_o + a) - T]$$
$$= t_o + (d_o - T) + a$$

$$t_2 = t_1 + (d_2 - T)$$
$$= t_1 + [(d_o + 2a) - T]$$
$$= t_o + [(d_o + a) - T] + [(d_o + 2a) - T]$$
$$= t_o + 2(d_o - T) + 3a$$

$$t_3 = t_2 + (d_3 - T)$$
$$= t_2 + [(d_o + 3a) - T]$$
$$= t_o + 2(d_o - T) + 3a + [(d_o + 3a) - T]$$
$$= t_o + 3(d_o - T) + 6a$$
$$\ldots$$
$$t_n = t_o + n(d_o - T) + a\sum_{i=1}^{n} i \quad n = 0, 1, 2, \ldots$$

Figure 4:
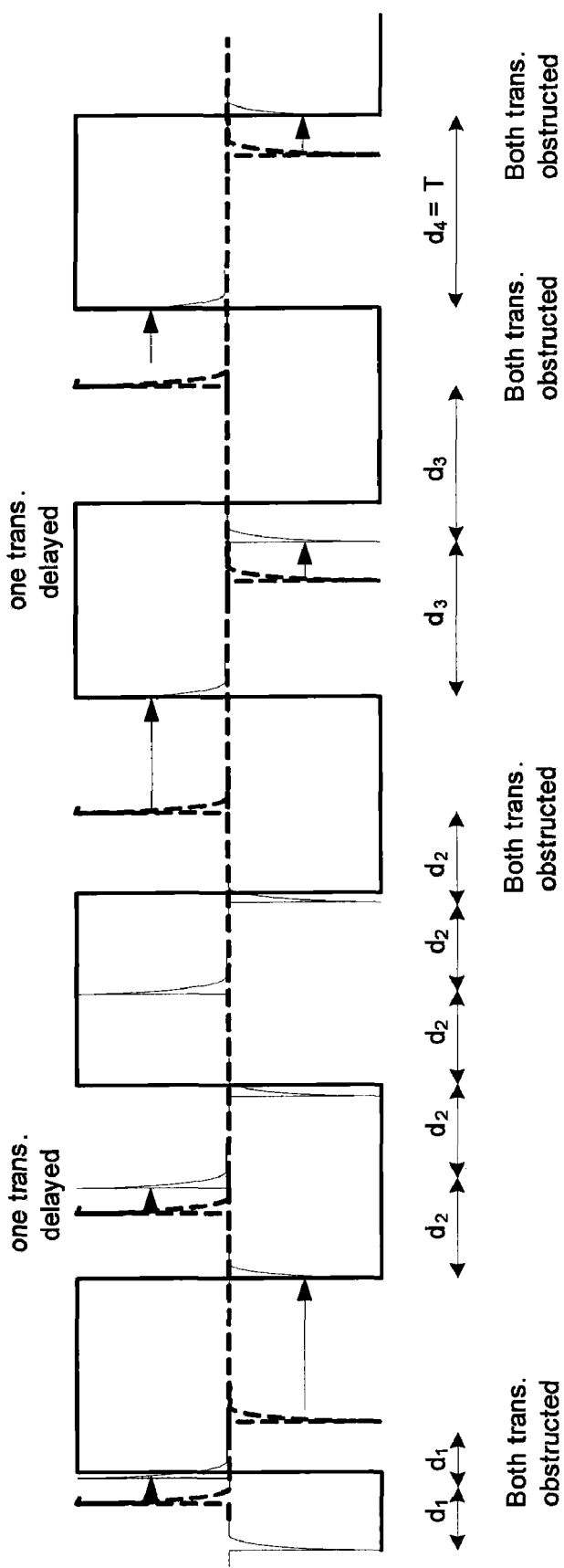
FIG. 4 is an image depicting the scenario when the pumping rate is much smaller than the field frequency (d<<T). As long as both transports fall into inhibiting half-pulses, Na extrusion into a negative half-pulse and K influx into the following positive half-pulse, the field significantly delays the two transports or increases the time interval d. Eventually, the d becomes equal to the half-pulse duration and the pumps having high pumping rates will be synchronized to the field frequency.

When the field-strength is very small so that a can be ignored and the third term eliminated, the phase-difference (second term) is accumulated up linearly due to initially $d_o>T$. The electric field accelerates the phase-accumulation so that the transport quickly falls into the following facilitating half-pulse (FIG. 4).

In summary for the first situation of Case 2, if the two transports initially fall into two hindering half-pulses, respectively, the electric field forces them further out of phase with respect to the hindering pulses so that both transports fall into the following facilitating half-pulses.

Figure 5:
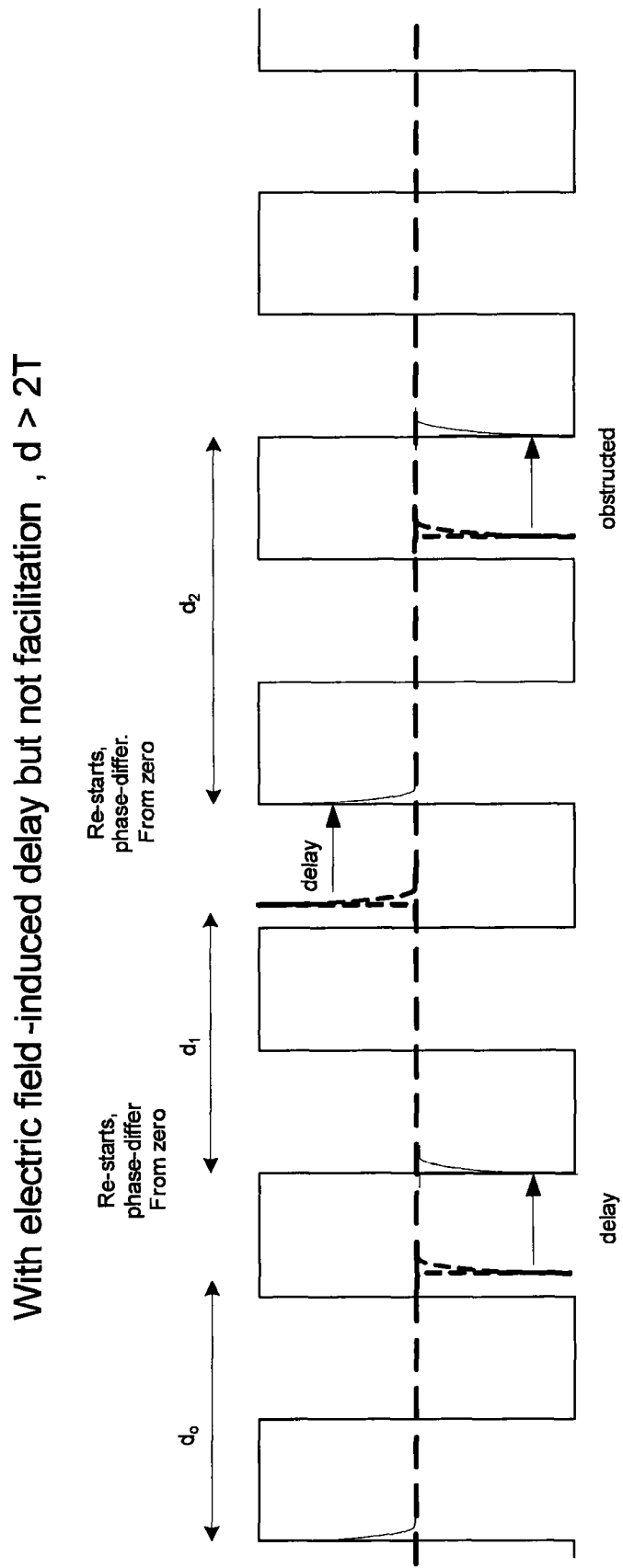
FIG. 5 is an image depicting pumping with field-induced delay but not facilitation. The time interval is much longer than the half-pulse duration, d>>T. The ion transport falling into an inhibiting half-pulse will be delayed until the following facilitating half-pulse. Therefore, the d will be increased slightly so that both ion transports fall into the succeeding facilitating half-pulses. When this is accomplished, d will no longer change.

When the two transports fall into the facilitating half-pulses alternately (the second situation), the field-effects will be significantly different. If the pumping rate is a little higher than the field frequency, or $T/2<d_o<T$, the phase-difference will be accumulated down in the succeeding half-pulses, $t_0>t_1>t_2>t_3>\ldots$, even the field-strength is very small (FIG. 5). The field-facilitation accelerates this down-accumulation. Again, for simplicity, assume that the facilitating effects on the two transports are similar and each facilitating-half-pulse reduces the time-interval d by a factor of b. The initial time-interval $d_o$ will be continuously reduced in the succeeding half-pulses. The phase-difference at the $n^{th}$ half-pulse will be:

$$t_1 = t_o - (T - d_1) \quad (3)$$
$$= t_o - [T - (d_o - b)]$$
$$= t_o - (T - d_o) - b$$

$$t_2 = t_1 - (T - d_2)$$
$$= t_1 - [T - (d_o - 2b)]$$
$$= t_o - [T - (d_o - b)] - [T - (d_o - 2b)]$$
$$= t_o - 2(T - d_o) - 3b$$

$$t_3 = t_2 - (T - d_3)$$
$$= t_2 - [T - (d_o - 3b)]$$
$$= t_o - 2(T - d_o) - 3b - [T - (d_o - 3b)]$$
$$= t_o - 3(T - d_o) - 6b$$
$$\ldots$$
$$t_n = t_o - n(T - d_o) - b\sum_{i=1}^{n} i \quad n = 0, 1, 2, \ldots$$

Again, the second term represents the down-accumulation of the phase-difference due to initially $d_o<T$, and the third terms represents the field-facilitating effects. When the number n increases, the phase-difference quickly reduces to zero, or the transient pump current catches the rising-phase of the pulse. The number of half-pulses needed is as follows:

$$0 = t_o - n(T - d_o) - b\sum_{i=1}^{n} i \quad (4)$$

When $T<d_o<2T$, the phase-difference can be expressed:

$$t_1 = t_o + (d_1 - T) \quad (5)$$
$$= t_o + [(d_o - b) - T]$$
$$= t_o + (d_o - T) - b$$

$$t_2 = t_1 + (d_2 - T)$$
$$= t_1 + [(d_o - 2b) - T]$$
$$= t_o + [(d_o - b) - T] + [(d_o - 2b) - T]$$
$$= t_o + 2(d_o - T) - 3b$$

$$t_3 = t_2 + (d_3 - T)$$
$$= t_2 + [(d_o - 3b) - T]$$
$$= t_o + 2(d_o - T) - 3b + [(d_o - 3b) - T]$$
$$= t_o + 3(d_o - T) - 6b$$
$$\ldots$$
$$t_n = t_o + n(d_o - T) - b\sum_{i=1}^{n} i \quad n = 0, 1, 2, \ldots$$

Figure 6:
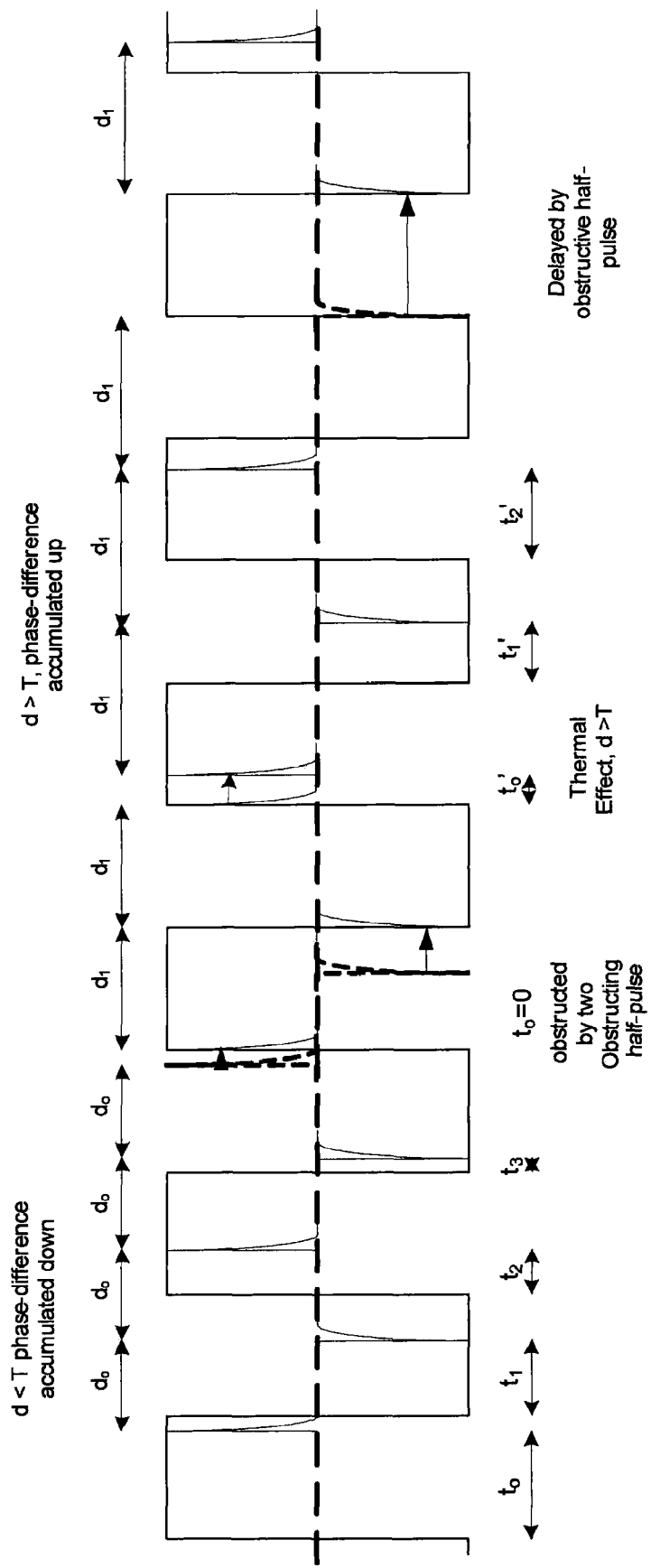
FIG. 6 is an image depicting phase difference accumulation in which the pumping rate is comparable to the field frequency, or T/2<d<T. The phase difference t is accumulated to be smaller and smaller. As long as the current catches the rising phase of the corresponding facilitating pulse, thermal effect-induced fluctuation will result in a new phase difference, which will be accumulated again.

The second and third terms have opposite signs. The second term represents the phase-difference up-accumulation due to initially $T<d_o$ while the third term represents the down-accumulation due to the field facilitation. The third term increases much faster by n(n+1)/2 than the linear increase of the second term as n increases (FIG. 6). The up-accumulation quickly becomes down-accumulation as long as the two terms equalize:

$$\frac{d_o - T}{n(d_o - T)} = \frac{1}{n}\sum_{i=1}^{n} i \quad (6)$$

Again, the transport will catch the rising phase of the facilitating half-pulses. In other words, the two ion-transports are kept within the facilitating pulses.

Where the ion-transport falls into the preceding half-pulse (a hindering half-pulse) the transports will be delayed until the pulse changes its polarity to a facilitating half-pulse. As a result, both transports will alternately be trapped in the consecutive facilitating half-pulses. Consequently, all individual pumps extrude Na ions during the positive half-pulses and pump in K ions during the negative half-pulses thus providing evidence that the pump molecules are synchronized to the oscillating electric field.

The field-induced hindering factor a and facilitating factor b are independent on the phase-difference $t_i$ because the electric field has a dichotomous waveform. The field-effects remain the same regardless of the position in the half-pulse in which the transport occurs. Factor a represents the hindering effects induced by each half-pulse for both the Na and K transports. Similarly, we assume that the same facilitating effect b for both the Na and K transports. Results based on these assumptions should not lose their generality in terms of understanding the underlying mechanisms involved in the pump synchronization. Further distinguishing the different field-effects on the two transports is useful when focusing on the quantitative study of how many pulses are needed to realize the synchronization.

Figure 7:
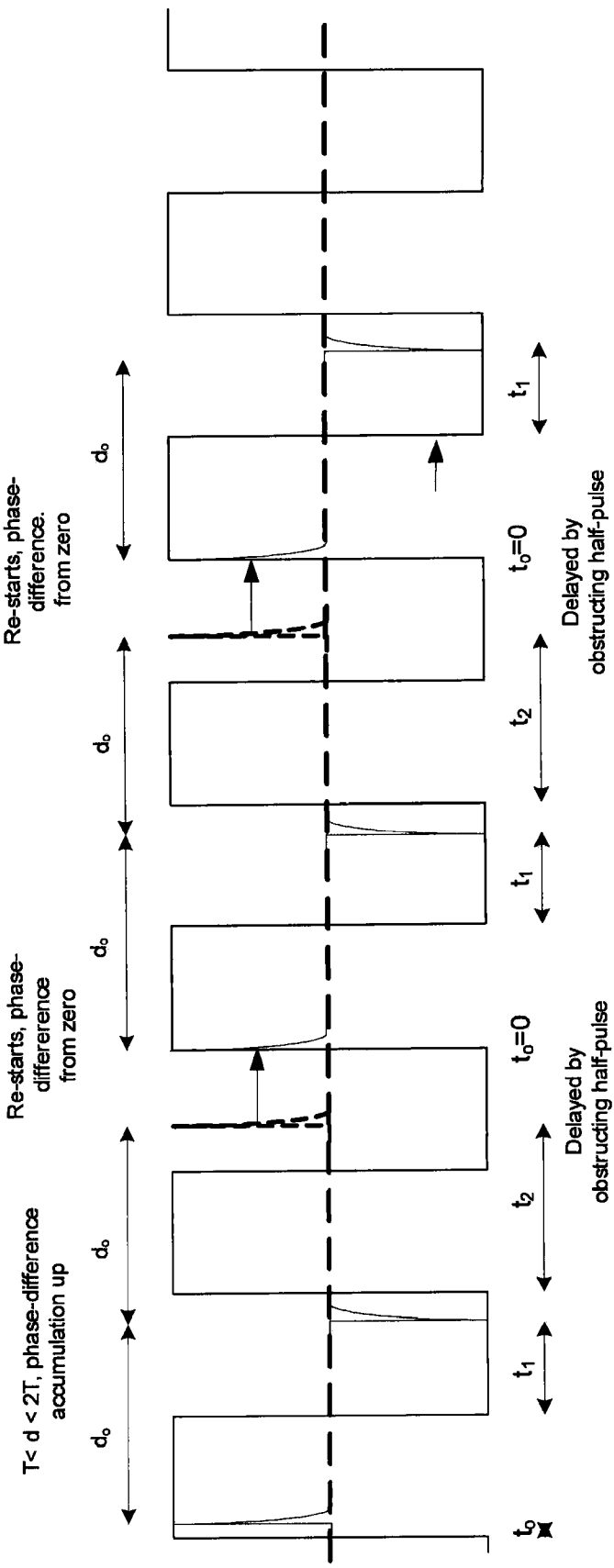
FIG. 7 is an image depicting phase difference accumulation in which the pumping rate is slightly higher than the field frequency, T<d<2T. The phase difference t is accumulated to become larger. Whenever a current falls into a following inhibitory half-pulse, the ion transport will be delayed until the facilitating half-pulse thus resulting in a zero phase difference. Because T<d<2T, two ion transports cannot both fall into inhibitory half-pulses. Therefore, the time interval d cannot become larger than 2T.

In Case 3, the initial pumping rate is much lower than the field oscillating frequency, or $d_o>2T$, which allows the patterns of the field-induced effects on the pump molecules to remain the same as above. The only difference is that the two transports cannot fall into two consecutive half-pulses due to the initial $d_o>2T$. Similarly, the electric field keeps the two ion-transports out of the corresponding hindering half-pulses. As a result, both the Na- and K-transports will be trapped into the corresponding facilitating half-pulses. For example, for a pump whose initial time-interval $d_i$ is in a range of $4T>d_o>2T$, if the Na-extrusion is trapped into a positive half-pulse, the following K-influx will be trapped in the second negative half-pulse, or the pumping rate is synchronized to one third of the field-frequency (FIG. 7). The pump molecules whose initial time-interval $d_o$ is much longer than the half-pulse duration or whose pumping rate is much lower than the field oscillating frequency, will be synchronized to a fraction of the field-frequency.

In summary for Case 3, due to the different effects of the two half-pulses of the oscillating electric field on the two ion-transports the two ion-transports of the individual pumps will be eventually kept in the consecutive facilitating half-pulses. Consequently, the pump currents elicited by the positive half-pulses mainly represent the outward Na-currents and those evoked during the negative half-pulses represent the inward K-currents.

Figure 8:
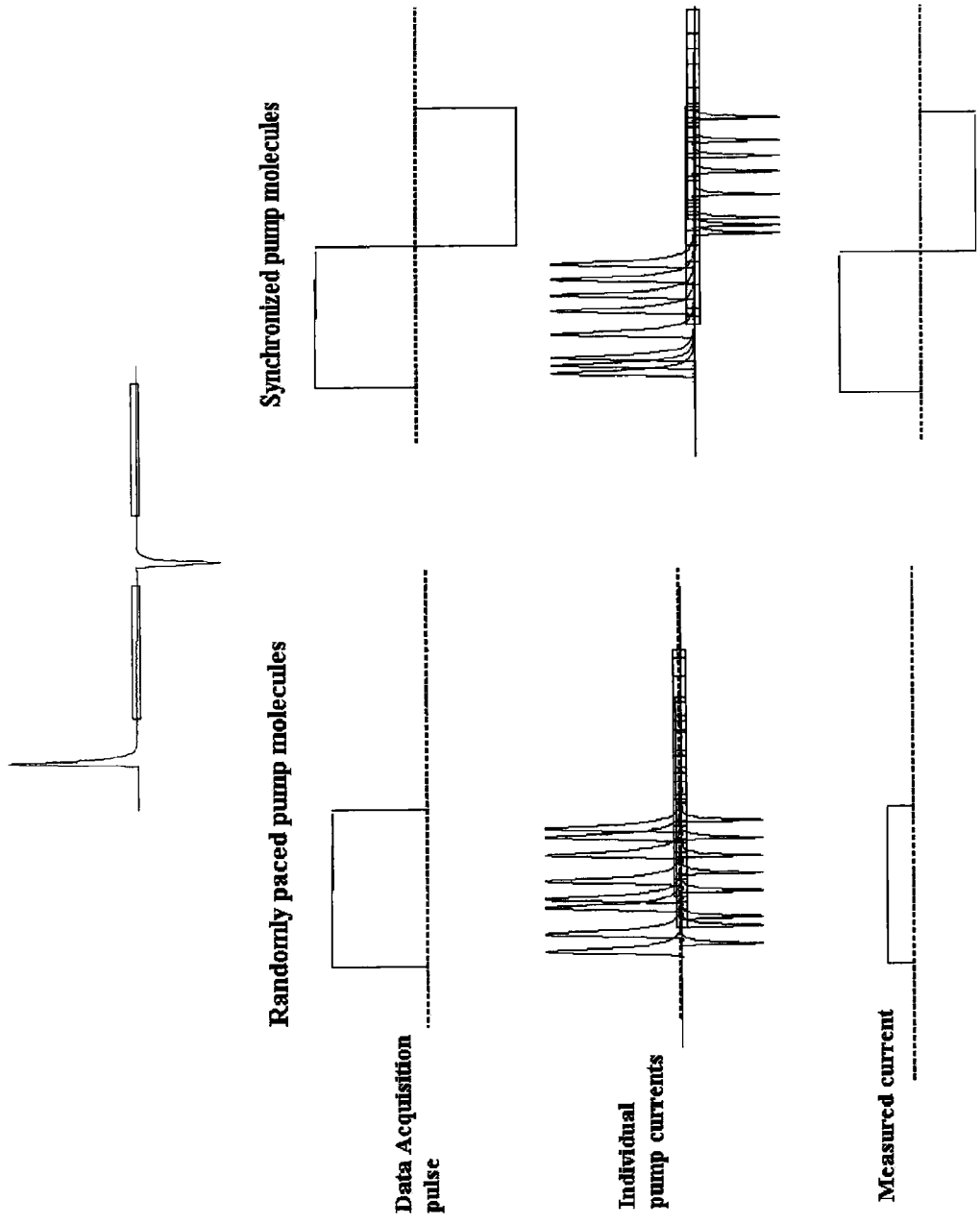
FIG. 8 is an image depicting the schematics of the Na/K pump currents. The upper panel shows the pump current elicited by a single Na/K pump molecule based on previous studies from other labs. The left column shows the pump currents from randomly paced pumps, and the right column shows the pump currents from synchronized pumps.

FIG. 8 illustrates the features of the measured pump currents from a group of synchronized and unsynchronized pumps. The two separated transient pump currents in the upper panel represent the two ion-transports of a pumping loop. Magnitude ratio of the two currents is 3:2 representing 3 Na and 2 K ions. Without synchronization, the inward K currents cannot be distinguished from the outward Na currents in a steady-state current measurement. The measured pump currents, which is a current summation from all the individual pumps, only exhibits a net outward current as shown in the left column of the lower panel. This is consistent with experimental results from many labs using voltage-clamp techniques. Once synchronized, all of the pumps extrude Na ions during the positive half-cycle and subsequently pump in K ions during the negative half-cycle. The two components of the pump currents are separated as shown in the right column of the lower panel. The magnitude ratio of the outward to inward currents remains 3:2 reflecting the pump's stoichiometric ratio of 3:2.

Synchronization

An oscillating electric field with a frequency comparable to the pumps' turnover rates can adjust the pumping rates and pumping phases of the individual pumps so that the Na-extrusion falls into the positive half-cycle and the K-influx falls into the negative half-cycle. Based on the above discussions, a pump molecule with a turnover rate in a range from one half to double of the field oscillating frequency can be synchronized to the field frequency. If the pump initial turnover rate is lower than this range, the Na-extrusion and K-influx will also be trapped into the positive and negative half-pulses, respectively, but not in the consecutive two half-cycles. However, even though all the individual pumps are synchronized to the oscillating electric field, their ion-transports are not static within the facilitating half-pulses because once the two transports are trapped into the corresponding two half-cycles, the field loses its capability to distinguish transports from individual pumps.

The phase-difference-accumulation can lead the pumping loop out of the phase from the oscillating electric field. The phase difference can be accumulated in the succeeding half-pulses. Alternatively, the field facilitation effects can move the transports toward the rising-phase of the facilitating half-pulses. Because the facilitation effects are more significant than the phase-difference-accumulation in the following pulses (Eq. 5), the ion-transports will be trapped in the facilitating half-pulse and eventually move towards the rising phase. Once reaching the preceding hindering half-pulse, the ion-transport will be hindered until the pulse changes its polarity, and returns to the facilitating half-pulses.

Furthermore, due to environmental changes, such as the ionic concentration changes induced by ion channel opening and thermal effects, the pumping rate can fluctuate thus resulting in new time-interval d and new phase-difference t. This fluctuation can happen at any time in the synchronization process. Some ion-transports may even fall into the following half-pulse, the hindering half-pulse, at which time the transport will experience competition of facilitation and phase-difference-accumulation again, and eventually be trapped in the facilitating half-pulses.

In order to explore the underlying mechanisms involved in synchronization of the ion transporters, the inventor employed a simple model of the carrier-mediated ion transporter or pump molecule, in this case the Na/K pump molecule, where all of the currents in the Na-extrusion limb are attributed in a single narrow pulsed current, and likewise for the K-influx limb. More than one step is electrogenic in each ion-transport limb. Previous studies of the Na/K pump have shown that there are at least two electrogenic steps in each transport limb. There are ion movements in both the binding access channel and the unbinding access channel. These are separated by intermediate steps which are voltage-independent. Therefore, even though the first current is close to the rising phase, the second one is not and may be spread in the half-pulse due to different time-courses of the intermediate voltage-independent steps.

In summary, synchronization of pump molecules is a dynamic process. Each individual pump tends to be out of phase with respect to the oscillating electric field due to phase-difference-accumulation. However, because of the stronger field-facilitating-effects, most of the pump molecules or at least most of the time of each individual pump will be trapped in the facilitating half-pulses. Whenever the field oscillation is ceased, the pumps quickly lose their synchronization and thus become randomly paced.

Voltage-dependence or I-V curve of the synchronized pumps as a function of the synchronization modulation electric field As long as the pump molecules are synchronized to the oscillating electric field, the frequency of the oscillating electric field can be gradually increased. If all the pumps can be kept synchronized during the frequency change, the pumping rates of the synchronized pump molecules will be progressively modulated to higher levels. Practically, once reaching synchronization the field frequency can be incrementally changed in small steps thus allowing the pumps to be re-synchronized to the new frequency. By increasing the field frequency in small increments, the turnover rate of the pump molecules can be gradually up-modulated in a stepwise pattern.

The synchronization and modulation of the pump molecules provides a novel method to organize and activate the pump molecules. As stated previously, the Na/K pump was used as an example of the process and did not involve any specific characteristics of the pump molecules thus other carrier-mediated ion transporters can be synchronized by a specially designed oscillating electric field.

In order to predict voltage-dependence of the synchronized ion-transporters, or I-V curve of the synchronized ion-transports as a function of the synchronization modulation electric field, the inventor again used the Na/K pumps as an example to explain the process of dynamic entrainment of the exchangers' turnover rate by the synchronization modulation electric field (Chen, W., 2006, Voltage-dependence of carrier-mediated ion transporters, *Physical review.* E, Statistical, nonlinear, and soft matter physics February; 73 (2 Pt 1): 021902-1-7. 2006; Chen, W., Electrical Synchronization of ion exchangers (submitted)).

Figure 9:
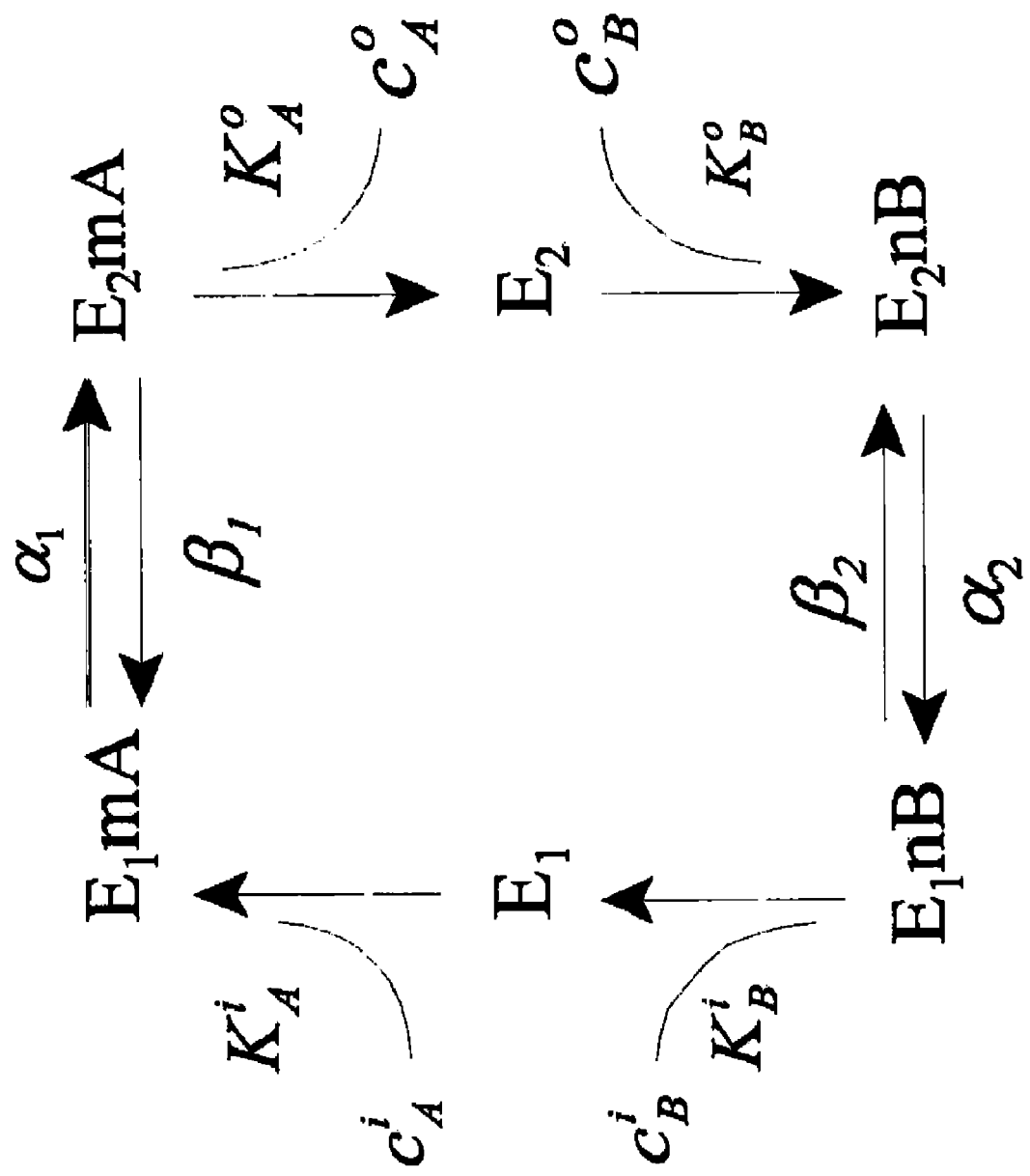
FIG. 9 is an image depicting a schematic drawing of an asymmetric 6-state model for the carrier-mediated ion-transporters based on experimental results. The model incorporates all of the voltage-dependent steps into two transitional steps. All other steps are voltage-independent. The two voltage-dependent steps, from $E_{1mA}$ to $E_{2mA}$ and from $E_{2nB}$ to $E_{1nB}$, represent the processes of ion-A-extrusion and ion-B-moving in steps, respectively. The word, "asymmetry" denotes different ion binding affinities at intracellular and extracellular sides of the membrane.

An asymmetric six-state model as shown in FIG. 9 is used where the binding and unbinding of two legends on the two sides of a cell membrane are separated. "Asymmetry" is defined as the transporters having different binding affinities to two legends on the two sides of a cell membrane. This arrangement allows the study of the field-effects on both ion-transports in the same loop. This six-state model has been successfully used to study the sigmoidal shaped I-V curves of the Na/K pumps (Rakowski et al, 1989) and the distribution of the pumping rates as a function of the environment parameters (Lauger 1986).

The field-effects on the ion-transport steps of an ion-transporter can be shown for an ion-transporter that transports m ions A out of the cell by exchanging n ions B into the cell in each cycle. In this situation, both ions, A and B, are cations, m is the number of ions transported out of the cell, and n is the number of ions transported into the cell. All of the voltage-dependent substeps are divided into two voltage-dependent steps: from $E_1$ to $E_2$ and from $E_2$ to $E_1$ in the loop. Four voltage-independent steps represent other processes which are insensitive to the membrane potential, including binding and unbinding steps with the legends such as ions and ATP (FIG. 9). The binding and unbinding steps are defined only in a chemical-reaction sense, not including the related conformational change in the protein such as occlusion and de-occlusion, which are involved in the voltage-dependent steps. The kinetic behavior of the six-state model can be written by six differential chemical reaction equations.

According to Boltzmann theory, each reaction rate is proportional to an exponential of the ratio of the energy difference associated with the ion translocation event over the thermal energy (KT). When a potential difference, V, is applied to the cell membrane, there are two kinds of energies that are involved in ion-transport: the intrinsic conformational energy of the transporter which is independent of the membrane potential and the electric energy supplied by the membrane potential, V.

Therefore, each reaction rate can be considered as a product of two parts. The first part, $\alpha_o$ and $\beta_o$ reflects the intrinsic energy. For active transporters, such as the Na/K pumps, the energy provided by ATP hydrolysis belongs to this intrinsic energy. The second part reflects the effects of the membrane potential, which can be expressed as follows:

$$\alpha_1 = \alpha_{1o}\alpha_{1V} = \alpha_{1o}e^{A_1V}$$

$$\beta_1 = \beta_{1o}\beta_{1V} = \beta_{1o}e^{-B_1V}$$

$$\alpha_2 = \alpha_{2o}\alpha_{2V} = \alpha_{2o}e^{-A_2V}$$

$$\beta_2 = \beta_{2o}\beta_{2V} = \beta_{2o}e^{B_2V} \qquad (7)$$

$$\alpha_{1V} = e^{A_1V}$$

$$\beta_{1V} = e^{-B_1V}$$

$$\alpha_{2V} = e^{-A_2V}$$

$$\beta_{2V} = e^{B_2V} \qquad (8)$$

where the parameters As and Bs are functions of the number of ions transported and the energy barriers involved in ion transport. It is necessary to point out that the ions A and B are moved in opposite directions, so that the membrane potential V has opposite effects on their forward reaction rates, $\alpha_1$ and $\alpha_2$, represented by the opposite signs in the exponentials. The same effects applied on their backward reaction rate $\beta_1$ and $\beta_2$. Through these arrangements, both passive and active transporters are covered in the model without loss of generality.

When an oscillating electric field V(t) such as a sinusoidal wave is applied to the cell membrane, the voltage-dependent parts of the reaction rates become:

$$\alpha_{1V} = e^{A_1V(t)}$$

$$\beta_{1V} = e^{-B_1V(t)}$$

$$\alpha_{2V} = e^{-A_2V(t)}$$

$$\beta_{2V} = e^{B_2V(t)} \qquad (9)$$

Therefore, the reaction rates are no longer constant but change as a function of time. When the field oscillating frequency is higher than the pumps' turnover rate, such as kilo- or mega-Hz, during each ion-transport the reaction rate $\alpha$ and $\beta$ will continue to oscillate.

A DC field can be applied so that the reaction rates become constants. When the DC field is applied to the system for a sufficient amount of time, the system reaches a steady-state. The general kinetic differential equations can be simplified to the following algebra equations:

$$\phi_1 = c_{E_1mA}\alpha_1 - c_{E_2mA}\beta_1 \qquad (10)$$

$$\phi_2 = c_{E_1nB}\beta_2 - c_{E_2nB}\alpha_2$$

$$\phi_1 + \phi_2 = 0$$

$$\sum_{i=6} c_i = c_{ET}$$

where $c_{E_1mA}$ is the concentration of the transporter at state $E_1$ binding m ions A, $c_{E_2mA}$ is the concentration of the transporter at $E_2$ binding m ions A, and so on. The first equation represents the protein's outwards flux $\phi_1$ from state $E_1$ to $E_2$ as a function of forward and backward reaction rates $\alpha_1$ and $\beta_1$. The second equation represents the influx $\phi_2$ from $E_2$ to $E_1$ as a function of reaction rates $\alpha_2$ and $\beta_2$ (FIG. 9). Since the transporter resides permanently within the membrane, the total flux must be zero, which is shown in the third equation. The fourth equation is the transporter conservation equation, where $c_{ET}$ is the total concentration of the transporter. In addition, the binding and unbinding processes at the membrane interfaces are rapid when compared with the rates of the two ion-translocations. Therefore, these processes can be considered to be at equilibrium, represented by their dissociation constants (Rakowski et al, 1989):

$$K_{mA}^{i}, K_{nB}^{i}, K_{mA}^{o}, K_{nB}^{o} \qquad (11)$$

where the subscripts represent binding (unbinding) of m ions A ions or n ions B, and the superscripts represent the two sides of the cell membrane (i=inside; o=outside). The detailed expressions of these dissociation constants and the flux $\phi$ have been obtained previously (Rakowski et al, 1989) as:

$$\phi = \phi_1 = -\phi_2 = c_{ET} \frac{C_5 \alpha_{1V} \alpha_{2V} - C_6 \beta_{1V} \beta_{2V}}{C_1 \alpha_{1V} + C_2 \beta_{1V} + C_3 \alpha_{2V} + C_4 \beta_{2V}}, \qquad (12)$$

where the parameters, Cs, are combinations of the ionic concentrations, the dissociation constants, and all of the voltage-independent parts of the reaction rates, $\alpha_{io}$ and $\beta_{io}$. The above parameters are not sensitive to the membrane potential. Only the forward and backward reaction rates, $\alpha_{iV}$ and $\beta_{iV}$, are sensitive to the membrane potential.

By substituting Eq. 8 into Eq. 12, we get:

$$\phi = c_{ET} \frac{C_5 e^{(A_1-A_2)V} - C_6 e^{-(B_1-B_2)V}}{C_1 e^{A_1 V} + C_2 e^{-B_1 V} + C_3 e^{-A_2 V} + C_4 e^{B_2 V}} \qquad (13)$$

Equation 13 describes pumping flux as a function of the membrane potential. The denominator is a weighted summation of all four reaction rates, where the parameters in the exponentials are $A_1$, $-B_1$, $-A_2$ and $A_2$, respectively. The numerator is a weighted subtraction in exponentials where the first term is a subtraction of $(A_1-A_2)$ and the second term of $-(B_1-B_2)$. When the two forward reaction rates and the two backward reaction rates are comparable, respectively, which is the case for many carrier-mediated ion-transporters such as the Na/K pump molecules, the results of the two subtractions are small. Therefore, the value of the first term cannot be particularly high, and the second term cannot be particularly small. As a result, the pumping flux cannot be significantly increased even when a large membrane potential, V, is applied to the cell membrane.

A DC change in the membrane potential, either depolarization or hyperpolarization, cannot significantly increase or decrease the pumping flux. The potential-sensitivity is low which restrains the effectiveness of electrical activation of the ion-exchangers. In order to increase the pumping flux, a large value of the numerator of Eq. 13 is needed which can be realized by increasing the first term and decreasing the second term.

Alternatively to DC application, a pulsed oscillating field can be applied. The two ion-transports do not occur at the same time but rather occur in a sequential pattern. This allows the two transports to be treated separately and sequentially. Moving cations in the opposite directions allows them to have reverse voltage-dependences. Applying a pulsed oscillating electric field whose frequency is comparable to the ion-exchanging rate and in which the oscillating pace matches the exchanging loop so that extruding ion-A during the positive half-pulse and then intruding ion-B during the negative half-pulse, allows the membrane potential to remain a constant in each corresponding ion-transport. Throughout the entire ion-A extrusion, the membrane potential is a positive constant and therefore the reaction rates, $\alpha_{1V}$ and $\beta_{1V}$, remain unchanged even though the membrane potential is oscillated. Similarly, during the ion-B influx, the membrane potential has a constant negative value and the reaction rates, $\alpha_{2V}$ and $\beta_{2V}$, remain unchanged:

$$\alpha_{1V} = e^{A_1 V}$$

$$\beta_{1V} = e^{-B_1 V}$$

$$\alpha_{2V} = e^{A_2 V}$$

$$\beta_{2V} = e^{-B_2 V} \qquad (14)$$

The expression of the reaction rates is very similar to that in Eq. 8 regarding a DC field application with the only difference being a change in the sign. When continuously exposed to this oscillating electric field, the ion-exchanger will quickly reach a steady-state. In the same way that the DC field application was treated, the same expression of flux $\phi$ of Eq. 12 is shown except the reaction rates in Eq. 14. By substituting the reaction rates Eq. 14 into Eq. 12, we have:

$$\phi_1 = c_{ET} \frac{C_5 e^{(A_1+A_2)V} - C_6 e^{-(B_1+B_2)V}}{C_1 e^{A_1 V} + C_2 e^{-B_1 V} + C_3 e^{A_2 V} + C_4 e^{-B_2 V}} \qquad (15)$$

In comparing Eq. 15 to Eq. 13, in the numerator the exponential parameter in the first term becomes $(A_1+A_2)$ V and that in the second term becomes $-(B_1+B_2)$ V. When the membrane potential, V, increases the value of the denominator does not change significantly. However, the numerator increases dramatically because the first term increases and the second term decreases. As a result, the pumping flux, $\phi$, can significantly increase as the membrane potential V increases.

The pumping process details must be considered in order to apply the synchronization modulation method to the Na/K pump. Three sub-steps are involved in each ion-translocation step: binding access channel or "ion well", changing protein conformation, and releasing access channel or "ion well" (Apell, 2003). Three apportionment factors (a, r and b) represent the three portions of the membrane potential (aV, rV, and bV) which impact the three sub-steps, respectively. In terms of the protein conformation change sub-step, there is an apportionment factor, h. Membrane potential, hrV, provides energy to overcome the energy barrier from $E_1$ to $E_2$ affecting the forward reaction rates $\alpha_1$ in the Na-transport and the backward reaction rate $\beta_2$ in the K-transport. The rest of portion, (1−h)rV, provides energy to overcome the energy barrier from $E_2$ to $E_1$ affecting the backward reaction rate $\beta_1$ in the Na-transport and the forward reaction rate $\alpha_2$ in the K-transport. Apportionment factors are used to retain generality and have been used previously (Rakowski et al, 1989).

Figure 10:
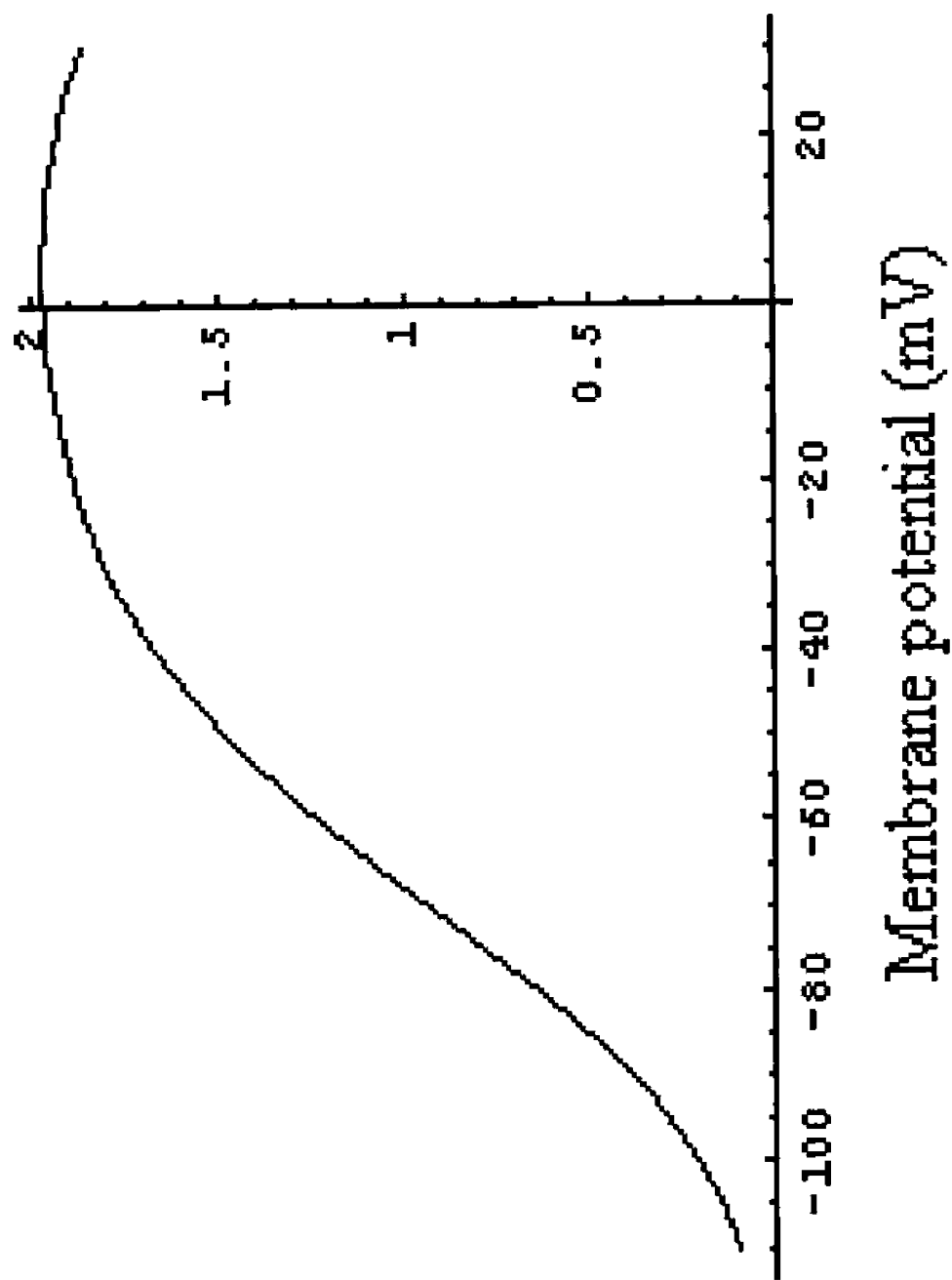
FIG. 10 is an image predicting the Na/K pumping flux as a function of the membrane potential. Abscissa is the membrane potential (mV), and the ordinate is the pumping flux (arbitrary unit).

Substituting these apportionment factors into the forward and backward reaction rates for the two ion-translocations, respectively, and considering that 3 Na ion are extruded and 2 K ion are pumped in for each cycle (Nakao and Gadsby, 1989; Rakowski et al, 1991), the equations become:

$$A_1 = [3a + (3+z)hr + 3b]/26$$

$$B_1 = [3a + (3+z)(1-h)r + 3b]/26$$

$$A_2 = [2a + (2+z)(1-h)r + 2b]/26$$

$$B_2 = [2a + (3+z)hr + 2b]/26, \qquad (16)$$

where z is the intrinsic charge of the pump molecule which moves during the conformation changes. The intrinsic charge has been well accepted as −2 for the Na/K pump molecule (Gadsby and Nakao 1989). The following relation was also used in deriving Eq. 13:

$$\frac{e}{KT} = \frac{F}{RT} \qquad (17)$$

where F is Faraday's constant and R is the gas constant. At a room temperature of 24° C., RT/F is approximately equal to 26 mV. Assuming parameters, a=b=1/5 and r=3/5, and substituting these rate coefficients into Eq. 16, and then into Eq. 13, the pumping flux can be calculated as a function of the membrane potential, as shown in FIG. 10, when a dc field is applied to the cell membrane (Rakowski et al, 1989). Abscissa is the membrane potential (mV), and the ordinate is the pumping flux (arbitrary unit). The curve has sigmoidal shape, exhibiting a shallow slope and saturation behaviour, and having possible negative slope at a large depolarized membrane potential (Rakowski et al, 1989). A membrane potential depolarization cannot significantly increase the pump currents. Furthermore, there exists an upper limit of the pump currents. When the membrane potential is further depolarized, the pump current will eventually decrease. These results are consistent with previous results, obtained either theoretically (Lauger and Apell, 1986) or experimentally (Rakowski et al, 1997).

Figure 11:
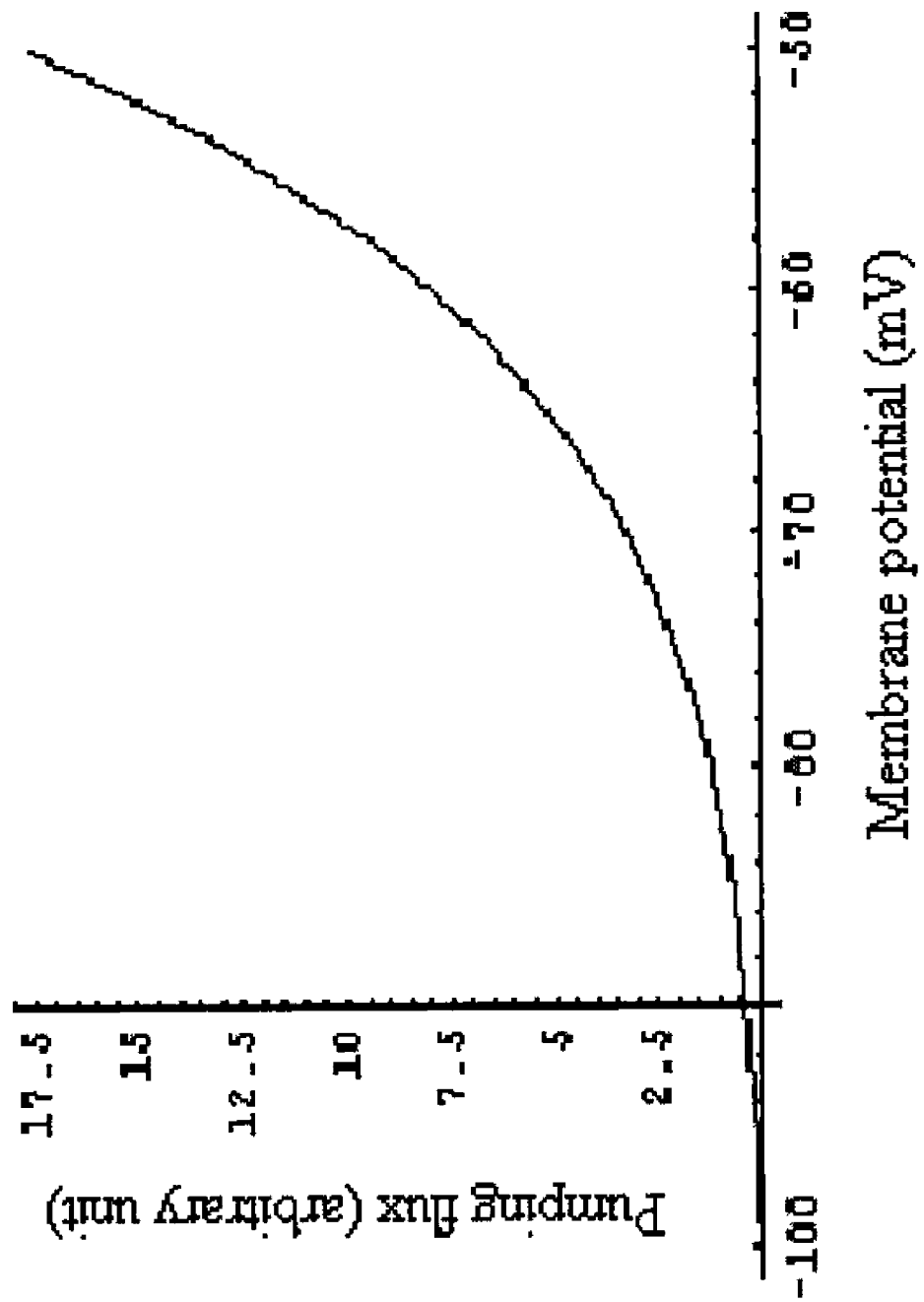
FIG. 11 is an image predicting pumping flux of the electrically synchronized Na/K pump molecules as a function of the membrane potential. All of the parameters are the same as those used in plotting the sigmoidal curve in FIG. 2.

In contrast, by substituting into Eq. 16 all of the parameters that were used to obtain FIG. 10 into Eq. 15, the pumping flux as a function of the membrane potential can be calculated. The result is shown in FIG. 11. Instead of showing a shallow sigmoidal curve with saturation behavior in FIG. 10, the pumping flux is significantly (exponentially) increased as a function of the membrane potential when a pulsed oscillating electric field, whose frequency is the same as the pump's turnover rate and is in phase with the pumping loop, is applied to the cells.

The pumping fluxes in response to a traditional DC change in the membrane potential and a special designed oscillating membrane potential can be compared since all of the parameters that were used to calculate the I-V curves shown in FIGS. 10 and 11 are the same. At the membrane resting potential of −90 mV, the pumping fluxes for both situations are the same, having a little less than 0.5 units (arbitrary units), as shown in FIGS. 10 and 11, respectively. When the membrane potential was depolarized to −50 mV, the pumping flux increased to a little less than 1.5 units, as shown in FIG. 10. However, the synchronization oscillating membrane potential can significantly increase the pumping flux to well above 15 units which is more than a 10-fold increase (FIG. 11). As the membrane potential further increases, the difference becomes even larger.

The underlying mechanism involved in the low sensitivity of the carrier-mediated ion-exchangers in the physiological situation showing a sigmoidal shaped I-V curve (Lauger and Apell, 1986) is mainly because the two ion-transports are in opposite directions, therefore having opposing voltage-dependence. Any DC change in the membrane potential, either depolarization or hyperpolarization, cannot facilitate both ion-transports. It can only facilitate one transport but inevitably hinder the other. Competition of the two opposite transports results in the sigmoidal I-V curve.

Exposure to the synchronization modulation electric field whose oscillating frequency matches the pumping loop allows the electric field to alternatively facilitate the two transports in the two half-pulses, respectively. For the Na/K pumps, the electric field can facilitate the Na-extrusion during the positive half-pulse and then facilitate the K-intrusion during the negative half-pulse, as shown in Eq. 15. The facilitation of each ion transport into corresponding half-pulses prohibits the two ion-transports from competing. Both transports are accelerated alternately by the electric field. As a result, the total pumping rate or the pump currents are significantly increased thus showing an exponentially-liked I-V curve.

Figure 12:
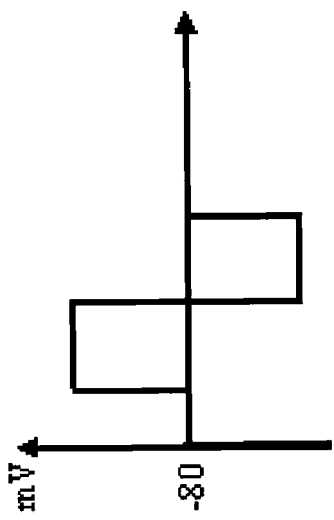
FIGS. 12A and B are images depicting increments in the pumping current by modulating the pumping rate. The half-pulse duration on the left is double of that on the right. When the pumps are initially synchronized to the left pulse and then modulated to the right pulse, the pump current doubles.
Figure 12:
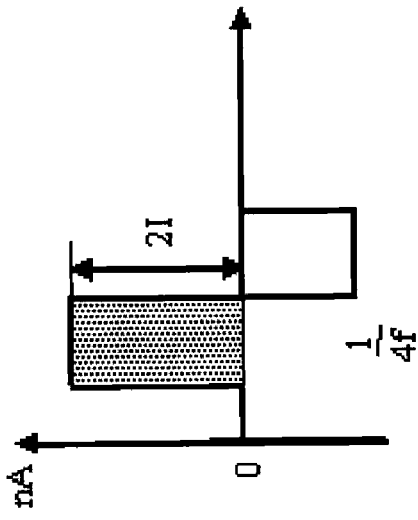
Figure 12:
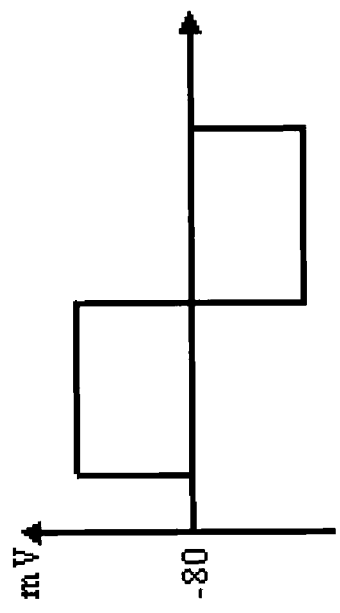
Figure 12:
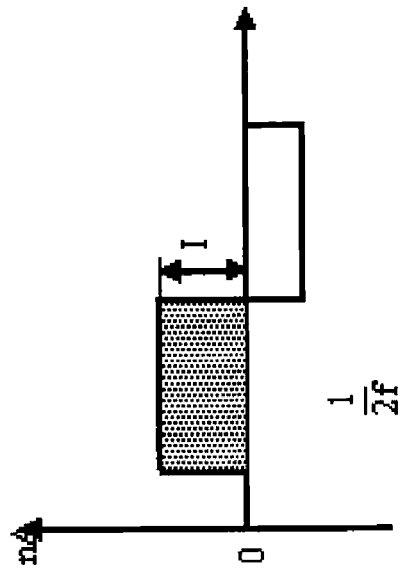

The pump currents responding to two synchronization frequencies can be compared. As shown in FIG. 12, the half-pulse duration shown on the left is double the half-pulse duration shown on the right. The magnitude of the pump currents corresponding to the right pulse should double that on the left because the same number of pump molecules are involved as well as the resulting same area of pump currents (shadowed).

In addition to the analysis, computer simulation to the pump synchronization was conducted (Chen, W. and Huang, F., Computer simulation of Synchronization of Na/K pump molecules, *Journal of Bioenergetics and Biomembrane*, August 5. [Epub ahead of print], 2008). Based on these studies, a series of whole cell voltage-clamp experiments was conducted to demonstrate the pump synchronization modulation (Chen W, Zhang Z S, Synchronization of Na/K pump molecules by a train of squared pulses. *Journal of bioenergetics and biomembranes* December; 38 (5-6):319-25, 2006; Chen, W., Zhang, Z. S. and Huang, F., Entrainment of Na/K pumps by synchronization modulation electric field, *Journal of Bioenergetics and Biomembrane* 39:331-339, 2007; Chen, W., Zhang, Z. S., and Huang, F., Synchronization of the Na/K pumps by an oscillating electric field, *Journal of Bioenergetics and Biomembrane*, August 2. [Epub ahead of print], 2008).

In addition to skeletal muscle fibers (Chen, W., and Dando, R., Electrical activation of Na/K pumps can increase ionic concentration gradient and membrane resting potential. *J. Membrane Biology,* 214:147-155, 2006; Chen, W., Dando, R., Synchronization modulation of Na/K pump molecules can hyperpolarize the membrane resting potential in intact fibers, *Journal of Bioenergetic and Biomembrane* 39:117-26. 2007), the synchronization modulation method has also been applied to mammalian cardiomyocytes (Chen, W., and Dando, R., Membrane potential hyperpolarization in mammalian cardiac cells by synchronization Modulation of Na/K Pumps, *Journal of Membrane Biology*, February; 221 (3): 165-73. 2008), and the PC-12 cell line (Chen, W., and Wang, L., Synchronization modulation of the Na/K pump molecules can hyperpolarize the membrane potential of PC 12 cells, Molecular and Cellular Biomechanics, V3 (4): 203-204, 2006). Furthermore, the synchronization modulation method has demonstrated therapeutic effects on electrically injured cells (Chen, W., and Dando, R., Cellular recovery from electroporation using synchronization modulation as rescue model for electrically injured cells, *Burns*, May 26. [Epub ahead of print], 2008).

The results have shown that the synchronization modulation method can effectively synchronize ion-transporters including carrier-mediated ion transporters such as the Na/K pump molecules, and significantly activate their pumping rate. Consequently, the method can transiently hyperpolarize the membrane potential and gradually increase the ionic concentration gradient. Even at non-physiological condition, the technique can promote the reinstatement of the physiological ionic concentration and membrane potential, and prevent cells from necrosis and cell death.

Given the criticality of carrier-mediated ion-transporters, particularly the Na/K pumps, to cell functions and disease, effectively controlling the pumping rate of ion-transporters can allow for the reinstatement of normal cell functions and reduction of symptoms of diseases that arise from malfunction of ion-transporters such as the Na/K pump. The Na/K pump, for example, has been implicated in diseases where a lack of ATP fails to fuel the pump molecules as in various cardiac diseases including murmurs, irregular heartbeat, and heart failure. The malfunction of the Na/K pumps as a result of a lack of ATP molecules is also implicated in brain ischemia and electrical injury where an intensive electrical shock generates pores in the cell membrane.

Diseases in which the density of the Na/K pump molecules in a cell membrane is significantly reduced can also be treated by controlling the Na/K pumps through the synchronization modulation method. Diseases in this category include myotonic dystrophy, diabetes, cystic fibrosis, central nervous system disorders, McArdle disease, and various neurological diseases such as Alzheimer's disease and Huntington's disease. The pump molecules in these diseases cannot maintain the ionic concentration gradients and membrane potential. Controlling the pump molecules through the synchronization modulation method would allow ionic concentration gradients to be maintained and thus would lessen symptoms of the disease. Furthermore, the method of synchronization modulation significantly activates pump functions and can compensate for a deficient number of pump molecules.

Other diseases characterized by a malfunction of the Na/K pump molecules include hypertension and diabetes. Dysfunction of the pump molecules can affect the kidneys, peripheral nerves, blood vessels, and muscle fibers. Research has been performed on various cell types including skeletal muscle fibers and cardiomyocytes. Application of the synchronization modulation method has exhibited a therapeutic effect on electrically injured cells. Similarly, for many wound healing processes including bone and skin healing, the Na/K pumps play a significant role in maintaining the healing process. By directly absorbing electric energy to activate the Na/K pump molecules, lessening of symptoms can be seen which significantly benefits patients with these diseases or conditions.

REFERENCES

Apell, H. J., 2003, Toward an understanding of ion transport through the Na, K-ATPases, *Ann. N.Y. Acd. Sci.*, 986:133.

Astumian, R. D., 1997, Thermodynamics and Kinetics of a Brownian motor, Science, V276:917.

Astumian, 2003, Physical Review letter, Adiabatic pumping mechanism for ion motive ATPases V91 (11)118102 (4).

Chen, W. and Lee, R. C., 1994, An improved double vaseline gap voltage clamp to study electroporated skeletal muscle fibers. *Biophysical Journal.* 66:700-709

Chen, W. and Wu, W. H., 2006, The asymmetric, rectifier-like I-V curve of the Na/K pump transient currents in frog skeletal muscle fibers, Bioelectrochemistry, 56:199-203

Chen, W., 2006, Voltage dependence of the carrier-medicated ion transporters, *Physical review.* E, Statistical, nonlinear, and soft matter physics February; 73 (2 Pt 1):021902-1-7

Chen, W., and Wang, L., 2006, Synchronization modulation of the Na/K pump molecules can hyperpolarize the membrane potential of PC 12 cells, Molecular and Cellular Biomechanics, V3 (4): 203-204

Chen W, Zhang Z S, 2006, Synchronization of Na/K pump molecules by a train of squared pulses. *Journal of bioenergetics and biomembranes* December; 38 (5-6):319-25

Chen, W., and Dando, R., 2006, Electrical activation of Na/K pumps can increase ionic concentration gradient and membrane resting potential. *J. Membrane Biology,* 214:147-155

Chen, W., Dando, R., 2007, Synchronization modulation of Na/K pump molecules can hyperpolarize the membrane resting potential in intact fibers, *Journal of Bioenergetic and Biomembrane* 39:117-26

Chen, W., Zhang, Z. S. and Huang, F., 2007, Entrainment of Na/K pumps by synchronization modulation electric field, *Journal of Bioenergetics and Biomembrane* 39:331-339

Chen, W., 2008, Synchronization of carrier-mediated pump molecules by an oscillating electric field: Theory, *Journal of Physical Chemistry B,* 112 (32), 10064-70

Chen, W., Zhang, Z. S., and Huang, F., 2008, Synchronization of the Na/K pumps by an oscillating electric field, *Journal of Bioenergetics and Biomembrane,* August 2. [Epub ahead of print]

Chen, W. and Huang, F., 2008, Computer simulation of Synchronization of Na/K pump molecules, *Journal of Bioenergetics and Biomembrane,* August 5. [Epub ahead of print]

Chen, W., and Dando, R., 2008, Membrane potential hyperpolarization in mammalian cardiac cells by synchronization Modulation of Na/K Pumps, *Journal of Membrane Biology,* February; 221 (3):165-73

Chen, W., and Dando, R., 2008, Cellular recovery from electrooration using synchronization modulation as rescue model for electrically injured cells, *Burns,* May 26. [Epub ahead of print]

Clausen, T., and Nielsen, O. B., 1998, Rapid activation of the Na/K pump: mechanisms and functional significance, Bio. Skr. Dan. Vid. Selsk., 49:153-158.

Clausen, T., 2003, Na/K pump regulation and skeletal muscle contractility, *Physiological Review,* 83:1269-1324.

De Weer, P., Gadsby, D. C., and Rakowski, R. F., 1988, Voltage dependence of the Na—K pump. Annu. Rev. Physiol. 50:225-241.

Gadsby, D. C., and Nakao, M., 1989, Steady-state current-voltage relationship of the Na/K pump in guinea pig ventricular myocytes. J. Gen. Physiol. 94:511-537.

Hille, B., 2003, Ionic channels of excitable membranes, $3^{rd}$ edition. Sinauer Associates Inc.

Kiernan, M. C., and Bostock, H., 2004, Effects of membrane polarization and ischaemia on the excitability properties of human motor axons. Brain; 123: 2542-51.

Lauger, P. and Apell, H-J. 1986, A microscopic model for the current-voltage behavior of the Na—K pump. Eur. Biophys. J. 13:309-321.

Lauger P., 1996, Na/K ATPase, in Electrogenic Ion Pumps, Sinauer, Mass., pp 201-204.

Liu, and Tsong, T. Y., 1990, The Journal of Biological Chemistry (1990) Vol. 265, No. 13: 7260-7267

Markin, V. S., Liu, D. S., Rosenberg, M. D., and Tsong, T. Y., 1992, Resonance transduction of low level periodic signals by an enzyme: an oscillatory activation barrier model, Biophysical, Journal, 61 (4):1045-1049.

Moldovan, M., and Krarup, C., 2006, Evaluation of Na/K pump function following repetitive activity in mouse peripheral nerve, J. Neuroscience Methods, 155:161-171

Nakao, M. And Gadsby, D. C., 1989, [Na] and [K] dependence of the Na/K pump current-voltage relationship in guinea pig ventricular myocytes, J. Gen. Physiol, 94:539-565.

Rakowski, R. F., Gadsby, D. C., and De Weer, P. 1989, Stoichiometry and voltage dependence of the sodium pump in voltage-champed, internally dialyzed squid giant axon. J. Gen. Physiol. 93:903-941.

Rakowski, R. F., Vasilets, L. A., Latona, J and Schwarz, W, 1991, A negative slope in the current-voltage relationship of the Na/K pump in *Xenopus* oocytes produced by reduction of external [K]. J. Membr. Biol. 121: 171-187.

Rakowski, R. F., Gadsby, D. C., and P. DeWeer, 1997, Voltage dependence of the Na/K pump, J. Membrane Biol. 155: 105-122.

Robertson, B., and Astumian, D., 1991, Frequency dependence of catalyzed reactions in a weak oscillating field, 1991, J. Chem. Phys. 94 (11):7414-7418.

Sejersted, O. M., and Sjøgaard, G., 2000, Dynamics and consequences of potassium shifts in skeletal muscle and heart during exercise. Physiol Rev 80: 1411-1481.

Serpersu, E. H., and Tsong, T. Y., 1983, *J. Membrane Biology*, 74:191-201.

Smith, K. J., Hall, S. M., 2001, Factors directly affecting impulse transmission in inflammatory demyelinating disease: recent advances in our understanding. Curr Opin Neurol, 14:289-98.

Tatsumi, H., and Katayama, Y., 1995, Na+ dependent Ca2+ influx induced by depolarization in neurons dissociated from rat nucleus basalis. Neurosci Lett, 196:9-12.

Teissie, J., and Tsong, T. Y., 1980, Evidence of Voltage-induced channel opening in Na/K ATPase of human erythrocyte membrane, J. Membrane Biol, 55, 133-140.

Tsong, T. Y., and Astumian, R. D., 1986, Absorption and conversion of electric field energy by membrane bound ATPases, Bioelectrochemi. Bioenerg. 13:457-476, 1986.

Tsong, T. Y., and Astumian, R. D., 1987, Electroconformational coupling and membrane protein function, Prog. Biophys. Molec. Biol. 50:1-45.

Tsong, T. Y., and Chang, C. H., 2003, Catalytic wheel, Brownian motor, and biological energy transduction, *AAPPS Bulletin*, 13 (2):12-18.

Waxman, S. G., 2005, Sodium channel blockers and axonal protection in neuroinflammatory disease. Brain, 128:5-6.

Xie, T. D., Marxzalek, P., Chen, Y. D., and Tsong, T. Y., 1994, Recognition and processing of randomly fluctuating electric signals by Na, K-ATPase, Biophysical Journal, (67) 1247-1251X.

Xie, T. D., Marszalek, P., and Tsong, T. Y., 1997, Fluctuation-driven directional flow in biochemical cycle: further study of electric activation of Na, K pumps, Biophysical Journal, (72):2496-2502.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

While there has been described a method of non-invasively and electrically controlling carrier-mediated ion transporters, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of controlling the cycle of a plurality of carrier-mediated ion transporters comprising the steps of:

applying an oscillating electric field at a predetermined synchronization frequency wherein the frequency is substantially equal to the ion transporters initial natural turnover rate; and incrementally adjusting the synchronization frequency to control the cycle.

2. The method of claim 1 wherein the carrier-mediated ion transporters have an ion-transport step that is the rate-limiting step to their respective reaction.

3. The method of claim 1 wherein the carrier-mediated ion transporters are sensitive to membrane potential.

4. The method of claim 1 wherein the magnitude of the oscillating electric field is restricted to a magnitude which allows the field-induced membrane potential to fall within the physiological range.

5. The method of claim 1 wherein the synchronization frequency of the oscillating electric field can be changed through changing oscillating cycle duration by applying continuous small changes in consecutive cycles or large incremental changes in repeating cycles.

6. The method of claim 5 wherein the changes in the oscillating cycle duration through applying small changes in consecutive cycles are about 1% or less of the cycle duration.

7. The method of claim 5 wherein the changes in the oscillating cycle duration through applying large incremental changes in repeating cycles are between about 3% and about 5% of the cycle duration.

8. The method of claim 5 wherein the maximum frequency incremental change is between half of the previous frequency and double the previous frequency.

9. The method of claim 5 wherein the maximum incremental change in the oscillating cycle is between half of the previous cycle duration and double the previous cycle duration.

10. The method of claim 1 wherein the turnover rate is reverse modulated when the synchronization frequency is gradually reduced.

11. A method of controlling the cycle of a plurality of Na/K pump molecules comprising the steps of:

applying an oscillating electric field at a predetermined synchronization frequency wherein the frequency is substantially equal to the pump molecules' initial natural turnover rate and;

incrementally adjusting the synchronization frequency to control the cycle.

12. The method of claim 11 wherein the magnitude of the oscillating electric field is restricted to a magnitude which allows the field-induced membrane potential to fall within the physiological range.

13. The method of claim 11 wherein the synchronization frequency of the oscillating electric field can be changed by changing pulse duration through applying continuous small changes in consecutive pulses or large incremental changes in repeating pulses.

14. The method of claim 13 wherein the changes in pulse duration by applying small changes in consecutive pulses are about 1% or less of the pulse duration.

15. The method of claim 13 wherein the changes in pulse duration by applying large incremental changes in repeating pulses are between about 3% and about 5% of the pulse duration.

16. The method of claim 13 wherein the maximum frequency incremental change is between half of the previous frequency and double the previous frequency.

17. The method of claim 13 wherein the maximum pulse duration is between half of the previous pulse duration and double the previous pulse duration.

18. The method of claim 11 wherein the pumping rate is reverse modulated when synchronization frequency is gradually reduced.

* * * * *